United States Patent
Karasawa et al.

(12) 
(10) Patent No.: US 7,421,900 B2
(45) Date of Patent: Sep. 9, 2008

(54) ULTRASONOGRAPH, ULTRASONIC TRANSDUCER, EXAMINING INSTRUMENT, AND ULTRASONOGRAPHING DEVICE

(75) Inventors: Hirokazu Karasawa, Yokohama (JP); Masayuki Nakamoto, Chigasaki (JP); Makoto Ochiai, Yokohama (JP); Katsuyoshi Fukuda, Yokosuka (JP); Taiji Hirasawa, Yokohama (JP); Takahiro Ikeda, Yokosuka (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 1192 days.

(21) Appl. No.: 10/398,874

(22) PCT Filed: Nov. 14, 2002

(86) PCT No.: PCT/JP02/11868

§ 371 (c)(1), (2), (4) Date: Apr. 10, 2003

(87) PCT Pub. No.: WO03/042686

PCT Pub. Date: May 22, 2003

(65) Prior Publication Data
US 2004/0024320 A1  Feb. 5, 2004

(51) Int. Cl.
*G01N 29/00* (2006.01)
*G01N 29/04* (2006.01)

(52) U.S. Cl. .............................. 73/621; 73/602; 73/633
(58) Field of Classification Search .................... 73/606, 73/602, 649, 653, 655, 656, 657, 621–625, 73/632–640
See application file for complete search history.

(56) References Cited

U.S. PATENT DOCUMENTS 3,600,935 A * 8/1971 Baum .......................... 73/603
4,317,369 A    3/1982 Johnson (Continued)

FOREIGN PATENT DOCUMENTS

EP           0 000 067         12/1978

(Continued)

OTHER PUBLICATIONS

Ogura, "The present Status of Non-destructive Inspection of Semiconductor Packages," Non-destructive Inspection, Japanese Society for Non-Destructive Inspection (May 2001), 50:290-292.

(Continued)

*Primary Examiner*—Helen C. Kwok
(74) *Attorney, Agent, or Firm*—Finnegan, Henderson, Farabow, Garrett & Dunner, L.L.P.

(57) ABSTRACT

An ultrasonograph, an ultrasonic transducer, an inspection device, and an ultrasonic imaging device enabling easy and quick inspection and high-resolution or high-speed processing are provided. Barium titanate ($BaTiO_3$) or lead zirconate titanate (PZT) is used for a piezoelectric material constituting the ultrasonic transducer, and the thickness thereof is 0.1 μm to 100 μm. Included therein are a drive section capable of driving an arbitrary one of piezoelectric layers, a detecting section detecting electrical signals generated by the plural piezoelectric layers based on echoes from an inspection object, the echoes being originated from an ultrasonic wave generated by the driven piezoelectric layer, and a processing section performing processing for visualizing a state of the inspection object based on the detected electrical signals.

1 Claim, 12 Drawing Sheets

U.S. PATENT DOCUMENTS

| | | | |
|---|---|---|---|
| 4,317,370 A | 3/1982 | Glenn | |
| 5,164,920 A | 11/1992 | Bast et al. | |
| 5,299,577 A | 4/1994 | Brown et al. | |
| 5,329,496 A | 7/1994 | Smith | |
| 5,339,282 A | 8/1994 | Kuhn et al. | |
| 5,369,624 A | 11/1994 | Fukukita et al. | |
| 5,377,006 A * | 12/1994 | Nakata | 356/486 |
| 5,406,163 A | 4/1995 | Carson et al. | |
| 5,479,259 A * | 12/1995 | Nakata et al. | 356/487 |
| 5,583,447 A | 12/1996 | Dascher | |
| 5,977,538 A * | 11/1999 | Unger et al. | 250/227.2 |
| 6,089,076 A * | 7/2000 | Mueller et al. | 73/24.06 |
| 6,095,978 A | 8/2000 | Takeuchi | |
| 6,159,149 A | 12/2000 | Erikson et al. | |
| 6,471,113 B1 | 10/2002 | Hirayama et al. | |
| 6,709,393 B2 * | 3/2004 | Ogawa | 600/443 |
| 2001/0041837 A1 | 11/2001 | Takeuchi et al. | |

FOREIGN PATENT DOCUMENTS

| | | |
|---|---|---|
| EP | 0 462 311 A1 | 6/1990 |
| JP | 54-18179 | 2/1979 |
| JP | 54-143194 | 11/1979 |
| JP | 55-14066 | 1/1980 |
| JP | 61-86651 | 5/1986 |
| JP | 61-210947 | 9/1986 |
| JP | 62-79157 | 4/1987 |
| JP | 62-112060 | 5/1987 |
| JP | 4-12452 | 3/1992 |
| JP | 4-198859 | 7/1992 |
| JP | 4-232425 | 8/1992 |
| JP | 5-1988 | 1/1993 |
| JP | 6-50744 | 2/1994 |
| JP | 7-46694 | 2/1995 |
| JP | 11-271285 | 10/1999 |
| JP | 2000-028589 | 1/2000 |
| JP | 2001-116732 | 4/2001 |
| JP | 2001-255310 | 9/2001 |
| JP | 2001-298795 | 10/2001 |

OTHER PUBLICATIONS

Supplementary Partial European Search Report dated Jun. 17, 2005, issued in European Patent Application No. EP 02780085.

Supplementary European Search Report issued by the European Patent Office for European Patent Application No. 02780085.3-2204, dated Aug. 23, 2005.

Korean Official Action issued by the Korean Patent Office for Korean Patent Application No. 2005-033586736, dated Jul. 15, 2005, and English-language translation thereof.

Havlice et al., "Medical Ultrasonic Imaging: An Overview of Principles and Instrumentation," Proceedings of the IEEE (Apr. 1979), 67:620-641.

Communication issued by the European Patent Office on Feb. 22, 2008, for European Patent Application No. 02 780 085.3.

* cited by examiner

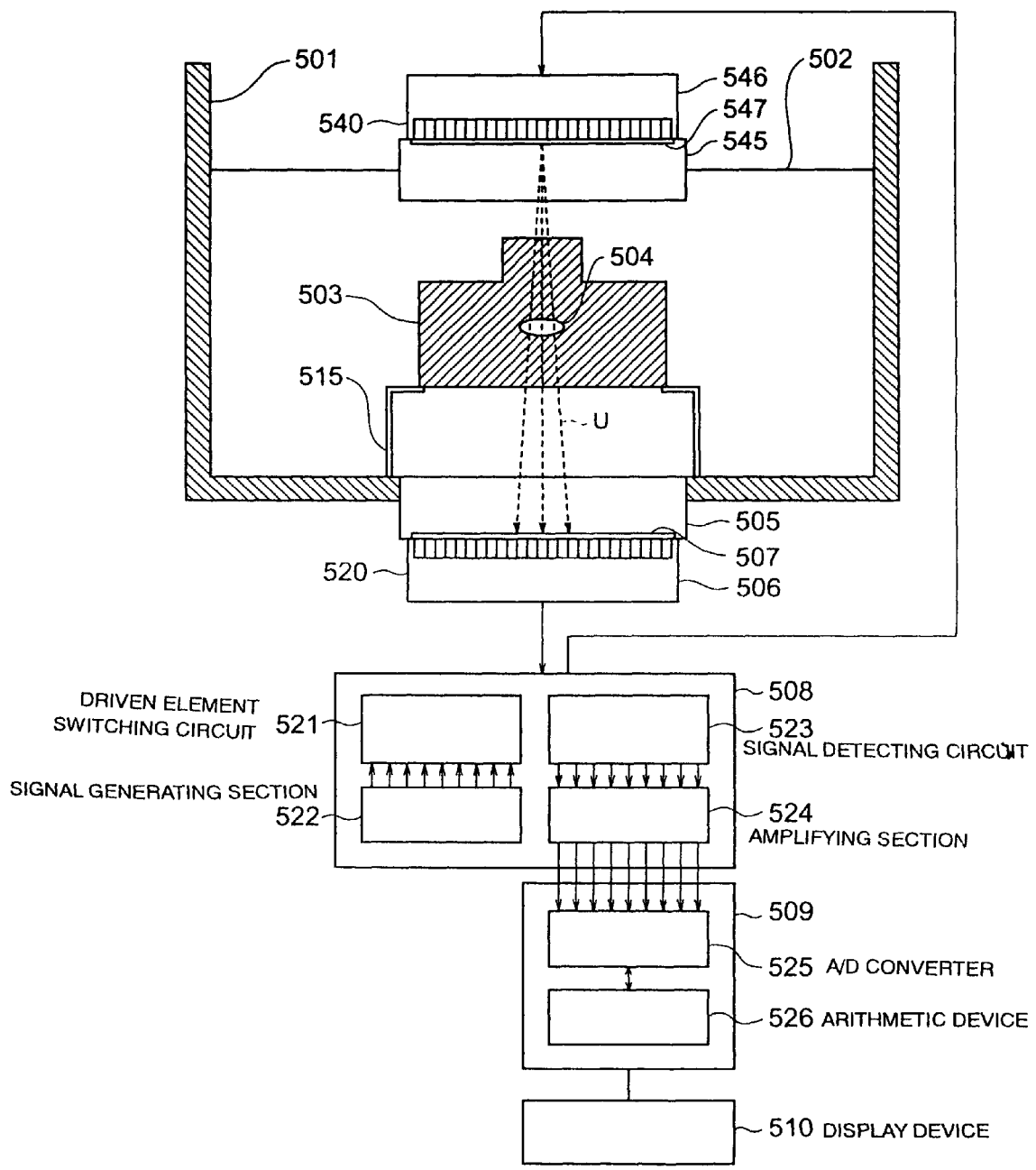

ULTRASONOGRAPH, ULTRASONIC TRANSDUCER, EXAMINING INSTRUMENT, AND ULTRASONOGRAPHING DEVICE

TECHNICAL FIELD

The present invention relates to an ultrasonograph which inspects abnormality such as internal defects and peel-off in semiconductor chips, metal, ceramic components, resin, and so on through the use of ultrasonic waves, and to an ultrasonic transducer, an inspection device, and an ultrasonic imaging device therefor, and more particularly, to the ultrasonograph, the ultrasonic transducer, the inspection device, and the ultrasonic imaging device suitable for use in easily and quickly inspecting the abnormality with enhanced precision or higher speed.

BACKGROUND ART

Ultrasonic inspection of microscopic internal structures of semiconductor chips (integrating circuits: IC) and so on is carried out for the purpose of inspecting the bonding state of solders which join functional faces of the semiconductor chips and wiring substrates, and of fillers filled in gaps therebetween and for other purposes.

Methods of such inspection include a method in which an inspection object is irradiated with ultrasonic waves via water from a monocular ultrasonic transducer while the transducer is mechanically scan-moved in the water, the ultrasonic waves returning as echoes after being propagated through the inspection object are captured by the above-mentioned transducer, and signals thus obtained are processed, thereby judging the state of the inspection object.

What is becoming a problem at present in such an inspection method is that the underwater mechanical scan takes a lot of trouble and time so that, in the case of a semiconductor chip or the like, the chip becomes unusable after the inspection, and further, that lack of an abnormality judging capability may possibly be caused with the present inspection precision since the area and pitch of connection terminals of a semiconductor chip which is to be an inspection object are made narrower.

The ultrasonic transducer as stated above, an essential part of which can be manufactured by processing a piezoelectric material such as zinc oxide and tin oxide into a film, requires to have a certain film thickness in light of securing detection sensitivity. However, in a practical point of view, securing a large film thickness gives restriction on an upper limit of a frequency of a generated ultrasonic wave. This leads to lack of the abnormality judging capability since the frequency is substantially correlated with resolution.

A film thickness may be small when a piezoelectric material with a high sensitivity is selected, and, though it is understood that a resultant increase in drive frequency enables a high resolution to be obtained, it is generally difficult to achieve uniform formation.

Meanwhile, an ultrasonic imaging device having a monocular ultrasonic sensor transmits ultrasonic waves in a vertical direction using, for example, an immersion method, to perform imaging of a specific focal depth on the premise that a reflector exists in front thereof. In this case, when the inspection object has a curved surface, such a problem arises that imaging of an internal part of the inspection object is not possible, and for example, the focus is not fixed to prevent high-precision imaging.

Further, an ultrasonic imaging device having an ultrasonic transducer constituted of a number of piezoelectric elements arranged in a matrix or in a line can at least realize high precision, but a large amount of processing in inspecting and visualizing internal defects, voids, peel-off, and so on poses a problem when an inspection object has a layered structure having a plurality of different acoustic features and has a curved surface. Such processing requires two-dimensional or three-dimensional refraction calculation of the propagation of many ultrasonic waves transmitted/received among the piezoelectric elements which are arranged in a matrix, thereby resulting in an enormous amount of processing time.

This being the situation, for example, when the layered structure and the surface shape of the inspection object can be specified, such a method can be utilized in order to shorten the processing time that propagation time of ultrasonic signals transmitted/received among a number of the piezoelectric elements which are arranged in a matrix or in a line is calculated in advance according to propagation routes such as refraction or the like to store the resultant propagation time in a tabular form. This eliminates the necessity of conducting the refraction calculation each time. Still in this case, however, a sufficient calculation speed is not achieved due to a large number of the piezoelectric elements.

Meanwhile, in the ultrasonic inspection by the immersion method, a piezoelectric element (a transmitter and receiver of ultrasonic waves) and an object to be inspected are immersed in liquid such as water, and ultrasonic waves are transmitted/received while the piezoelectric element is mechanically scan-moved to visualize an inner part of the object to be inspected (refer to the following paper).

Ogura, "The Present Status of Non-destructive Inspection of Semiconductor Packages", Non-destructive Inspection, Japanese Society for Non-Destructive Inspection, May 2001, Vol. 50, No. 5, p 291-292.

However, the piezoelectric element is immersed in the liquid in the immersion method so that durability thereof is liable to get low due to the intrusion of the liquid into the piezoelectric element. Moreover, it has been difficult to inspect the inner part of the object to be inspected disposed inside a hermetic container from an external part.

DISCLOSURE OF THE INVENTION

The present invention is made in consideration of the above circumstances, and an object thereof is to provide an ultrasonograph which inspects, using ultrasonic waves, abnormality such as peel-off of a connection part of the inside of a semiconductor chip, a composite material, and so on, and an inner defect of metal, and an ultrasonic transducer, an inspection device, and an ultrasonic imaging device therefor, and more particularly, an ultrasonograph, an ultrasonic transducer, an inspection device, and an ultrasonic imaging device which enable easy, quick inspection and an increase in resolution or processing speed.

In order to solve the above problem, an ultrasonograph according to an aspect of the present invention comprises: an ultrasonic transducer having a substrate, a common electrode formed on the substrate, a plurality of piezoelectric layers formed independently in a matrix on the common electrode, and a plurality of upper electrodes formed on the piezoelectric layers respectively; a drive section connected to the upper electrodes and capable of driving an arbitrary one of the piezoelectric layers via the upper electrode; a detecting section connected to the upper electrodes and detecting from the plural upper electrodes electrical signals that the plural piezoelectric layers generate based on reflected echoes from an inspection object, the echoes being originated from an ultrasonic wave generated by the driven piezoelectric layer; and a processing section performing processing for visualizing a state of the inspection object based on the detected electrical signals, each of the piezoelectric layers of the ultrasonic transducer including barium titanate (BaTiO$_3$) or lead zirconate titanate (PZT) and having a thickness of 0.1 μm to 100 μm.

This means that as a material of the piezoelectric layer film, barium titanate or lead zirconate titanate is used. Since these materials have a large electromechanical coupling factor compared with zinc oxide, and exhibit a high transducing efficiency between an electrical energy and a mechanical vibration energy, they are suitable for generating and detecting ultrasonic waves. Further, since they have a larger dielectric constant compared with zinc oxide, they exhibit excellent electrical matching with an electric pulse power source, for example, when they are pulse-driven.

The film is formed to have a thickness of 0.1 μm to 100 μm, utilizing the aforesaid high transducing efficiency. This makes it possible to heighten a frequency of an ultrasonic wave that the piezoelectric layer generates, for example, to about 20 MHz so that a sufficient resolution can be achieved. More practically, the film is preferably formed to have a thickness of about 0.5 μm to about 30 μm.

Incidentally, when barium titanate is used as a piezoelectric material, since Curie temperature thereof is slightly lower (about 130° C.) compared with lead zirconate titanate, it is more preferable that the Curie temperature is artificially increased, utilizing distortion due to mismatching of a lattice constant, when it is in use.

As a depositing method for forming the piezoelectric layer of barium titanate or lead zirconate titanate, physical vapor deposition such as a sputtering method, a solution coating method such as a sol-gel method, a chemical vapor deposition method such as MOCVD (metal organic chemical vapor deposition), and so on are usable. Such a piezoelectric film may be a polycrystalline film or an epitaxially-grown film, but it is more preferable to equalize crystal orientations through the use of epitaxial growth or the like since a higher piezoelectric transducing property is obtainable. Further, as another forming method, the piezoelectric film may be thinned in advance to the above-mentioned predetermined thickness, and methods of polishing and cutting work are usable for this processing. In this case, the piezoelectric material having been thinned by polishing or the like can be made to adhere onto the common electrode by a predetermined method (to be described later).

As materials of the common electrode and the upper electrode, precious metal such as Pt and Ir, a film of conductive oxide such as SrRuO$_3$, or the like can be named. The conductive oxide such as SrRuO$_3$ has a disadvantage of having a slightly higher electrical resistance compared with precious metals while having a characteristic that it is not easily peeled off mechanically because of a good coherent property of the interface thereof with the piezoelectric film as described above. For forming the electrodes, for example, sputtering is usable.

As a method of forming the plural piezoelectric elements in a matrix through the use of a piezoelectric thin film forming technique, the piezoelectric film may be deposited only on desired regions using a mask at the time of film growth by, for example, sputtering, or unnecessary parts of the film may be removed by a method such as chemical etching after the film is deposited over the entire surface. In general, the method using chemical etching is more preferable since it can achieve more microscopic processing with higher dimension precision.

An ultrasonic transducer according to another aspect of the present invention comprises: a substrate; a semiconductor integrated circuit formed on the substrate; a common electrode formed on a rear face of the substrate; and a plurality of piezoelectric layers independently formed in a matrix on the common electrode; and a plurality of upper electrodes formed on the piezoelectric layers respectively, each of the piezoelectric layers including barium titanate or lead zirconate titanate and having a thickness of 0.1 μm to 100 μm.

This ultrasonic transducer is so structured that the structure of the ultrasonic transducer in the aforesaid ultrasonograph is formed on a rear face of a semiconductor chip having an integrated circuit formed on a functional surface thereof. Most of the previous explanation applies to this ultrasonic transducer. Incidentally, when the area of the piezoelectric member is set, for example, to about 500 μm×500 μm or smaller, it can sufficiently cope with downsizing of terminals whose abnormality is to be detected.

An inspection device according to still another aspect of the present invention comprises: a plurality of contact terminals having a needle-like structure; a drive section connected to the contact terminals and causing an arbitrary one of the contact terminals to generate a drive voltage; a detecting section connected to the contact terminals and detecting from the plural contact terminals electrical signals which are returned from an inspection object to the contact terminals due to the generated drive voltage; and a processing section performing processing for visualizing a internal state of the inspection object based on the detected electrical signals and a position of the arbitrary contact terminal.

This inspection device, when combined with the aforesaid ultrasonic transducer, is capable of performing ultrasonic inspection. Signals are transmitted/received between the upper electrodes of the ultrasonic transducer and the inspection device through the contact terminals having the needle-like structure. Therefore, such combination can achieve a sufficiently high resolution in the ultrasonic inspection, similarly to the above explanation.

Incidentally, as the contact terminals, for example, field emission cold cathodes having sharp tips, or more preferably, cold cathodes by a transfer molding method are usable. These electrodes can realize a sufficient electrical contact state with the upper electrodes having a small area. In the case when the inspection device is combined with the aforesaid ultrasonic transducer, the contact terminals are provided so as to correspond to the respective upper electrodes of the ultrasonic transducer.

An ultrasonograph according to yet another aspect of the present invention comprises: an ultrasonic transducer having a common electrode including one surface, a piezoelectric layer formed on the one surface of the common electrode, and an upper electrode formed on the piezoelectric layer; a drive section connected to the upper electrode and capable of driving the piezoelectric layer via the upper electrode; a detecting section connected to the upper electrode and detecting from the upper electrode an electrical signal that the piezoelectric layer generates based on a reflected echo from an inspection object, the echo being originated from an ultrasonic wave generated by the driven piezoelectric layer; a scan-moving mechanism scan-moving the ultrasonic transducer relatively to the inspection object; and a processing section performing processing for visualizing a state of the inspection object based on the detected electrical signal and a position of the scan-moved ultrasonic transducer, the piezoelectric layer of the ultrasonic transducer including barium titanate or lead zirconate titanate and having a thickness of 0.1 μm to 100 μm.

This ultrasonograph does not use an ultrasonic transducer constituted of piezoelectric layers formed in a matrix but detects the state of the inspection object by mechanical scanning of the ultrasonic transducer itself. A characterizing portion of the piezoelectric layer of the ultrasonic transducer is almost the same as explained above.

An ultrasonograph according to yet another aspect of the present invention comprises: a laser beam source generating an intermittent or intensity-modulated laser beam; an optical transmitter irradiating an inspection object with the generated laser beam in a spot-like state; a scan-moving mechanism scan-moving the optical transmitter relatively to the object; a vibration displacement detecting section which performs non-contact detection of vibration displacement on a surface of the inspection object by a displacement measuring method using a laser beam, the vibration displacement caused by an echo of an ultrasonic wave in the inspection object generated by the irradiated laser beam, and which transduces the detected vibration displacement to an electrical signal; and a processing section performing processing for visualizing a state of the inspection object based on the electrical signal obtained after the transducing and a position of the scan-moved optical transmitter.

This ultrasonograph irradiates the inspection object with the intermittent or intensity-modulated laser beam in a spot-like state, thereby achieving a high resolution. The spot-like state laser beam enables the formation of an ultrasonic wave generating source with an extremely small area at an accurate position of the inspection object. Therefore, high-resolution detection is made possible by capturing the echo thereof.

An ultrasonic imaging device according to yet another aspect of the present invention comprises: an ultrasonic transducer having a plurality of piezoelectric elements arranged in a matrix or in a line; a driven element selecting section connected to the plural piezoelectric elements and capable of driving an arbitrary one of the plural piezoelectric elements; a signal detecting circuit connected to the plural piezoelectric elements and detecting in parallel electrical signals that the plural piezoelectric elements generate as a result of receiving, from an inspection object via an acoustic propagation medium, reflected echoes of an ultrasonic wave generated by the driven piezoelectric elements; a signal processing section performing processing for imaging a state of the inspection object by using parallel computation based on the electrical signals detected in parallel; and a display device displaying an imaged result of the processing, the signal processing section comprising: a storage section which stores ultrasonic wave propagation time from the driven piezoelectric element to one of the plural piezoelectric elements regarding each mesh in an area to be imaged in the inspection object, which is divided into meshes, the ultrasonic wave propagation time being stored for each combination of the driven piezoelectric element and the one of the plural piezoelectric elements; a plurality of processing sections using the stored ultrasonic wave propagation time to select a proper datum from one of the electrical signals detected in parallel, processing for determining a reflection intensity for each mesh in the area divided into meshes, the determining processing being performed in parallel for the electrical signals detected in parallel; and an adding section adding, for each mesh in the area divided into meshes, the reflection intensities determined by the parallel processing.

To summarize, as a precondition, the ultrasonic imaging device according to an aspect of the present invention uses, for generating and detecting ultrasonic waves, the ultrasonic transducer having the plural piezoelectric elements arranged in a matrix or in a line respectively. Arbitrary one of the plural piezoelectric elements is driven, the reflected echoes from the inspection object are detected in the plural piezoelectric elements and transduced to the electrical signals, the transduced electrical signals are detected in parallel in the signal detecting circuit, and parallel computation is further carried out in the signal processing section so that imaging processing is performed.

In the parallel computation, the aforesaid storage section, plural processing sections, and adding section are used. The storage section stores the ultrasonic wave propagation time from the driven piezoelectric element to one of the plural piezoelectric elements regarding each mesh in the area to be imaged in the inspection object, which is divided into meshes, the ultrasonic propagation time being stored for each of the combinations of the driven piezoelectric element and the one of the plural piezoelectric element.

The plural processing sections use this stored ultrasonic propagation time to perform the processing for determining the reflection intensity for each mesh in the area divided into meshes, based on one of the electrical signals detected in parallel, the determining processing being performed in parallel for the electrical signals detected in parallel. Such parallel processing enables fast processing. The processed results for each of the meshes in the area divided into meshes are added by the adding section. This makes it possible to obtain imaging data.

Incidentally, the storage section, the plural processing section and the adding section use, for example, a specialized or a general-purpose computer as hardware, and can be constituted of this hardware, and basic software and application software operating on this hardware.

An ultrasonograph according to yet another aspect of the present invention comprises: a piezoelectric section having a plurality of piezoelectric elements; a solid acoustic propagation medium in a flat plate shape acoustically connected to the piezoelectric section; a drive section selecting the piezoelectric element from the piezoelectric section to cause the selected piezoelectric element to generate an ultrasonic wave; a detecting section detecting electrical signals generated from the piezoelectric elements of the piezoelectric section based on reflected ultrasonic waves which result from reflection of a part of the ultrasonic wave from an object to be inspected in a liquid acoustic medium after the ultrasonic wave is transmitted from the piezoelectric element selected by the drive section; an image creating section creating an image showing an inner state of the object to be inspected based on the electrical signals detected in the detecting section; and a display section displaying the image created in the image creating section.

The plural arranged piezoelectric elements are electronically selected to perform transmission/reception so that visualization without any mechanical scanning is made possible. Moreover, the solid acoustic propagation medium is made to pass through a container which accommodates the object to be inspected therein and stores the liquid acoustic medium, or is connected acoustically to an outer surface thereof so that an external shape and an inner structure of the object to be inspected in the container can be visualized while the piezoelectric elements are kept disposed outside the container.

Here, "to be acoustically connected" represents a state allowing acoustic transmission between different acoustic media. Incidentally, when a couplant is interposed between the acoustic media, an acoustic transmission property between the different acoustic media can be improved.

BRIEF DESCRIPTION OF DRAWINGS

FIG. 12 is a schematic diagram showing an ultrasonograph according to an eighth embodiment of the present invention.

BEST MODE FOR CARRYING OUT THE INVENTION

Figure 1:
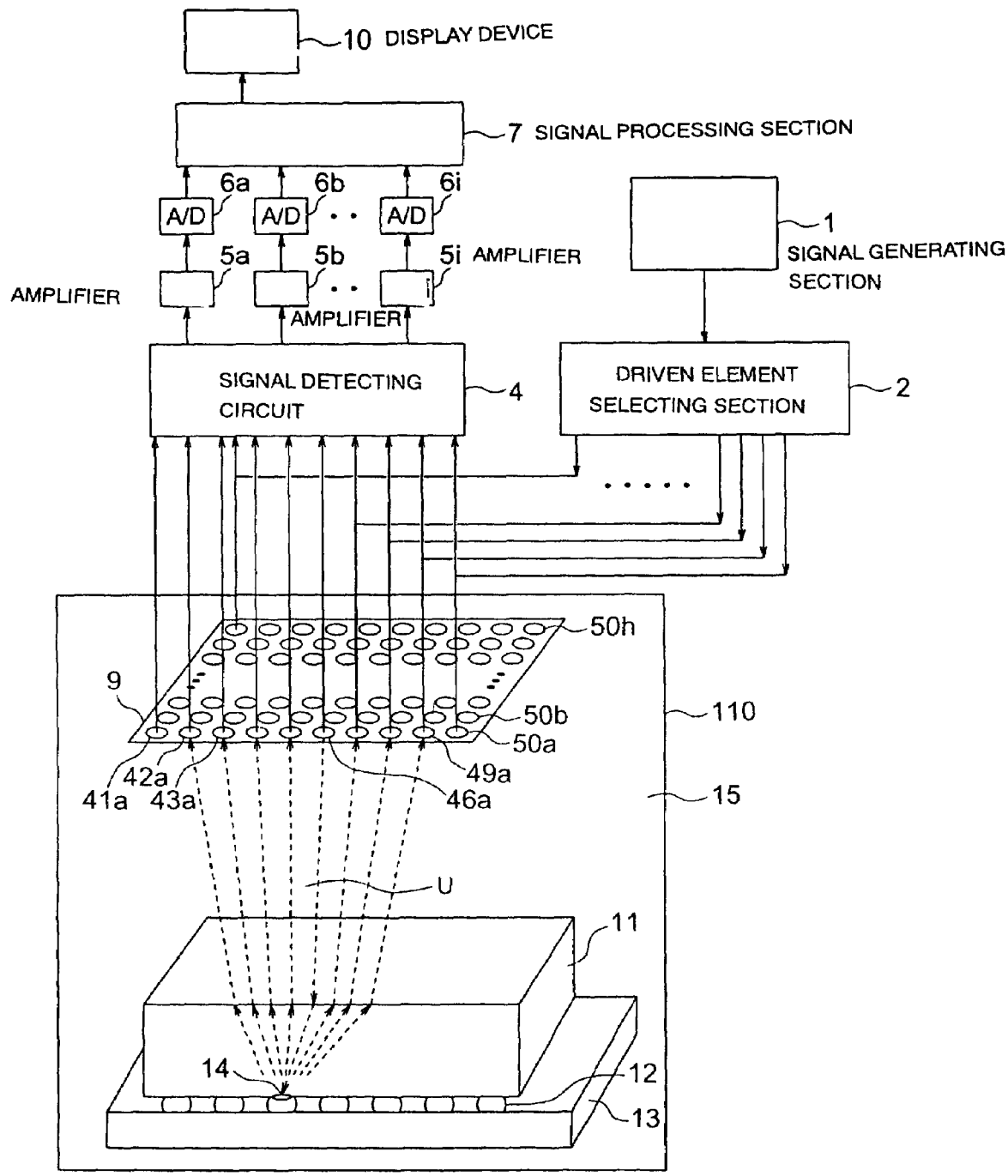
FIG. 1 is a block diagram explaining the configuration of an ultrasonograph according to a first embodiment of the present invention.

According to embodiments of the present invention, high-resolution ultrasonic nondestructive inspection can be realized easily and quickly thanks to characteristics of the structure and material of an ultrasonic transducer. Further, according to the embodiments of the present invention, since an ultrasonic wave generating source with an extremely small area can be formed on a surface of an inspection object, high-resolution ultrasonic inspection can be realized.

As a mode of the present invention, an ultrasonograph further comprises: a container which is capable of accommodating liquid and allows the ultrasonic transducer and the inspection object to be immersed in the accommodated liquid. As an acoustic medium, for example, water, which has a more excellent ultrasonic wave transmission property than gas, is used.

As another mode of the present invention, the processing section of the ultrasonograph calculates refraction of the ultrasonic wave, which occurs on an interface between an acoustic medium and the inspection object, to specify an ultrasonic wave route within the inspection object. This is intended for coping with a case when the acoustic medium is made of different substance from that of the inspection object (irradiation object).

As still another mode of the present invention, an ultrasonograph further comprises: a couplant provided on a rear face of the substrate of the ultrasonic transducer and allowed to be interposed between the substrate and the inspection object. This eliminates the necessity of immersing the substrate and the inspection object in water so that efficient and easy irradiation of the ultrasonic wave is possible. At this time, the couplant keeps the inspection object and the substrate free from stains and scratches, and the couplant can be easily removed from the inspection object. Moreover, when the substrate and the inspection object use the same materials (for example, silicon, epoxy, ceramic, metal, and the like), the influence of the refraction between the transducer and the inspection object is small to simplify signal processing.

For the couplant, liquid such as water and alcohol, a fibrous mesh material saturated with water or alcohol, a flexible organic material, ceramic, a metal material, and the like are usable. The use of the couplant having a thickness sufficiently smaller than a wavelength of the ultrasonic wave used for the inspection is preferable since it gives only a small influence to the inspection.

As yet another mode of the present invention, the common electrode of the ultrasonic transducer has a surface compound layer on an interface with the piezoelectric layer formed thereon. This surface compound layer functions as an adhesive layer between the common electrode and the piezoelectric layer. When the piezoelectric material is formed in advance through film thinning by polishing and cutting work, stable adhesion with the common electrode is required in subsequent steps. For this purpose, the surface compound layer is utilized.

An electrostatic adhesion method is used for forming the surface compound layer, and for an electrostatic adhesive layer, usable are, for example, glass (preferably, glass having mobile ions), water glass, $SiO_2$, Al, Ta, Ti, Ni, Si, Mo, Cr, Ge, Ga, As, Kovar, Fe, Mg, beryllium, and so on. This layer preferably has a thickness of 1 to 100 atom layers. This is because adhesiveness is saturated when the thickness exceeds 100 atom layers.

Further, it is preferable that surface roughness of the piezoelectric material at the time of the adhesion is set to 1% or lower of the thickness thereof (0.1 μM to 100 μm, more preferably, 0.5 μm to 30 m), and surface roughness of the adhesive layer to be the surface compound layer is similarly set since this will improve cohesiveness, resulting in stable adhesion.

Moreover, instead of using the electrostatic adhesion method, the substrate (common electrode) and a polarized piezoelectric layer may be made to adhere to each other by electrostatic attraction caused by the polarization, which makes it possible to easily obtain a flat adhesion state to the common electrode. In this case, when a metal layer formed by a sputtering method is formed on the piezoelectric layer, the cohesiveness is further enhanced. Further, post-processing in which the piezoelectric material is processed into the polarized state after the piezoelectric material and the common electrode are made to adhere to each other also has an advantage that an upper electrode can be stably formed on the piezoelectric material. Moreover, this can also prevent degradation of sensitivity and resolution due to undulation of the piezoelectric layer and unequal thickness of the surface compound layer.

Further, according to embodiments of the present invention, higher-speed processing is made possible by parallel processing.

As yet another mode of the present invention, the signal processing section of the ultrasonic imaging device has, in place of the storage section, a second storage section which generalizes transmitting-side ultrasonic wave propagation time from a piezoelectric element and receiving-side ultrasonic wave propagation time to a piezoelectric element regarding each mesh in an area to be imaged in the inspection object, which is divided into meshes, to thereby store the transmitting-side ultrasonic wave propagation time and the receiving-side ultrasonic wave propagation time for common use, and the plural processing sections use, in place of the stored ultrasonic wave propagation time, the stored transmitting-side ultrasonic wave propagation time and the stored receiving-side ultrasonic wave propagation time.

Such a second storage section is provided so that necessary memory areas can be greatly reduced. This structure is applicable to a case, for example, when the inspection object has a planar surface, and so on.

As yet another mode of the present invention, in the storage section of the signal processing section, the area to be imaged is limited in consideration of directivity of ultrasonic wave generation in the plural piezoelectric elements. Setting such limitation enables the reduction in memory areas unnecessary for processing.

Yet another mode of the present invention is so structured that, in the second storage section of the signal processing section, the area to be imaged is limited in consideration of directivity of ultrasonic wave generation in the plural piezoelectric elements. In this case, the memory areas unnecessary for processing can be also reduced.

In yet another mode of the present invention, the signal processing section further comprises: a propagation intensity characteristic storage section which stores an ultrasonic wave propagation intensity characteristic from the driven piezoelectric element to one of the plural piezoelectric elements regarding each mesh in the area to be imaged in the inspection object, which is divided into meshes, the ultrasonic wave propagation intensity characteristic being stored for each combination of the driven piezoelectric element and the one of said plural piezoelectric elements, and the plural processing sections of the signal processing section use the stored ultrasonic wave propagation intensity characteristics for correction in the processing for determining the reflection intensity.

The ultrasonic wave propagation intensity characteristic from the driven piezoelectric element to one of the plural piezoelectric elements varies depending on the directivity of the piezoelectric elements. For example, sensitivity degradation occurs in an ultrasonic wave transmitted or received at an oblique angle. Therefore, an amount of such sensitivity degradation is corrected by the propagation intensity characteristic stored in the propagation intensity characteristic storage section, thereby improving precision of a result of imaging. Incidentally, the propagation intensity characteristic storage section may be additionally provided in a storage section of ultrasonic wave propagation time using common addresses.

In yet another mode of the present invention, the signal processing section further comprises: a propagation intensity characteristic storage section which generalizes a transmitting-side ultrasonic wave propagation intensity characteristic from a piezoelectric element and a receiving-side ultrasonic wave propagation intensity characteristic to a piezoelectric element, to thereby store the transmitting-side ultrasonic wave propagation intensity characteristic and the receiving-side ultrasonic wave propagation intensity characteristic for common use, for each mesh in the area to be imaged in the inspection object, which is divided into meshes, and the plural processing section of the signal processing section use the stored transmitting-side ultrasonic wave propagation intensity characteristic and the receiving-side ultrasonic wave propagation intensity characteristic for correction in the processing for determining the reflection intensity.

In this case, an amount of the sensitivity degradation is also corrected by the propagation intensity characteristic stored in the propagation intensity characteristic storage section, thereby improving precision of a result of imaging. Here, in the propagation intensity characteristic storage section, necessary memory areas are greatly reduced. This structure is applicable to a case, for example, when the inspection object has a planar surface, and so on.

In yet another mode of the present invention, the signal processing section further comprises a data supplying section which supplies the storage section with data of the ultrasonic wave propagation time as an initial value; a section which detects a discontinuous surface or a discontinuous line of the inspection object based the reflection intensity for each mesh in the area divided into meshes, the reflection intensity obtained through the processing performed by the plural processing section using the supplied ultrasonic wave propagation time data for the inspection object and through the addition performed by the adding section; and a section which resets contents in the storage section based on the detected discontinuous surface or discontinuous line.

According to such a structure, for example, when a numerical value is given to the ultrasonic wave propagation time as the initial value on assumption that an inspection object is constituted of a single layer, the discontinuous surface or the discontinuous line of the inspection object can be detected from the obtained reflection intensity. In other words, an actual positional change of the inspection object (inspection object not including an acoustic propagation medium) can be found. When the ultrasonic wave propagation time is stored again according to this positional change, high-precision imaging is possible.

The following description gives an idea of an embodiment (sixth embodiment) of the present invention which will be described later.

In order to perform 3D image synthesis, for example, by aperture synthesizing, it is necessary to relate a waveform of an ultrasonic echo transmitted/received between two piezoelectric elements (time direction data) to a distance direction. Specifically, each sampling data of the ultrasonic echo waveform is converted to distance data according to a sonic velocity to specify a mesh to be imaged on which the ultrasonic wave is reflected, and the sampling data is related to the specified mesh to be imaged. Then, processing of adding the aforesaid sampling data (intensities represented by amplitude values) on all the combinations of the two piezoelectric elements is performed for all the meshes in a 3D imaged area or all the meshes in the area limited by a directional angle, so that a 3D image can be depicted.

Here, when the inspection is conducted, ultrasonic waves are generally transmitted/received to/from the inspection object in water or via an acoustic propagation medium made of a resin shoe material. Accordingly, in a propagation route of the ultrasonic wave, there exist at least regions where sonic velocities are different from each other, namely, the acoustic propagation medium and the inspection object. When the inspection object consists of a plurality of layers where sonic velocities are different, this results in a layered structure having three layers or more totally.

In the case of the plural layered structure, it is necessary to depict the 3D image by adding the sampling data (amplitude values) according to a two-way distance calculated in consideration of the refraction on an interface of each of the layers. Therefore, refraction calculation is generally performed for each mesh, and based on the results thereof, the sampling data are related to each mesh and are added so that an enormous amount of processing is required and it takes too long a time before the results are displayed, which makes it difficult to achieve performance suitable for practical use.

However, in the inspection by means of a shoe member with a fixed shape and the immersion inspection under a fixed condition, when the propagation time data is tabularized, this data can be utilized without any refraction calculation for each mesh. The tabularization can reduce the processing corresponding to the refraction calculation to memory access time. Further, when arithmetic circuits are provided in parallel for the plural receiving-side piezoelectric elements respectively, the processing speed of the image synthesizing is further increased.

Here, according to the above method, when, for example, 10×10 piezoelectric elements are arranged two-dimensionally in a matrix, it is necessary to prepare table data corresponding to all the combinations of two piezoelectric elements (transmitting-side, receiving side) out of 100 piezoelectric elements. Accordingly, when the interfaces of the above plural layers are complicated in shape, calculation time and data volume in preparing the table data in advance turn out to be enormous.

When the interface of the inspection object has a symmetric property or uniformity, to make the table data commonly usable without depending on the above combinations is very effective for reducing the calculation time and the data volume. For example, when a planar inspection object is inspected by a shoe member in a planar shape and with a fixed thickness, it is possible to calculate by coordinate transformation the propagation distance of transmission and reception from/to an arbitrary piezoelectric element, only with single table data corresponding to a one-way route of the ultrasonic wave. Consequently, memory size inside the parallel arithmetic circuits is reduced to further increase the processing speed thanks to fast access.

Further, when, at the time of preparing the table data of the ultrasonic wave propagation time and the common table data, regions of the table data are limited in consideration of the directivity of the piezoelectric elements, unnecessary imaging data are not depicted and efficiency in the image synthesizing can be enhanced.

Moreover, when, at the time of preparing the table data of the ultrasonic wave propagation time and the common table data, sensitivity distribution data according to the directivity are stored in addition to the propagation time in the table data in consideration of the directivity of the piezoelectric elements, it is possible to adjust a gain of an oblique component of an ultrasonic wave whose sensitivity gets low, thereby making effective use of echo data of the oblique component effective for improving precision.

Further, when, at the time of preparing the table data of the ultrasonic wave propagation time and the common table data, a single layer of an acoustic propagation medium made of a solid or liquid is assumed as the inspection object and initial setting for the table data is made for this inspection object, the resultant imaging makes it possible to extract a boundary surface between the acoustic propagation medium and the true inspection object. Then, with table data recalculated using this processing result, it is possible to cope with imaging in the case when the position varies. Further, in case the true inspection object has a complicated shape, shape data can be stored in advance so that the table data of the ultrasonic wave propagation time and the common table data can be reset in consideration of this stored shape data.

Moreover, embodiments of the present invention makes it possible to provide an ultrasonograph capable of detecting the state of an object to be inspected disposed inside a hermetic container from an external part without immersing piezoelectric elements (ultrasonic transducer) in liquid. This results in durability improvement since the piezoelectric elements are not immersed in liquid.

An ultrasonograph as a mode of the present invention is so structured that an array transducer in which piezoelectric elements are arranged in a matrix or in a line is fixedly in close contact with a shoe member via a couplant. This shoe member is connected to an outer surface of an inspection container embracing a liquid acoustic medium, or passes through an opening portion of the inspection container. As a result, it is possible to conduct inner inspection by collecting electrical signals of reflected ultrasonic waves or transmitting ultrasonic waves from the object to be inspected disposed in the inspection container and by synthesizing a visualized image from the collected data.

Here, when the position of a surface of the object to be inspected in the inspection container, namely, the piezoelectric element and a surface (interface) of the object to be inspected are known, a sonic velocity of the liquid acoustic medium in the inspection container is calculated based on the propagation time of the reflected ultrasonic wave from the time when it is sent from the piezoelectric element to the time when it reaches the piezoelectric element after being reflected from this interface, and this acoustic velocity is used for correction in image creating processing, thereby enabling precision improvement of image data.

Further, the installation of a reflector for changing an ultrasonic wave transmission angle in the inspection container enables measurement and visualization of the object to be inspected from a horizontal direction.

Hereinafter, embodiments of the present invention will be explained with reference to the drawings.

First, the embodiments of the present invention will be explained, taking the inspection of a semiconductor chip for example.

FIRST EMBODIMENT

FIG. 1 is a block diagram explaining the configuration of an ultrasonograph according to a first embodiment of the present invention. As shown in this drawing, this ultrasonograph has an ultrasonic transducer 9, a signal generating section 1, a driven element selecting section 2, a signal detecting circuit 4, amplifiers 5a, 5b, . . . , 5i, A/D converters 6a, 6b, . . . , 6i, a signal processing section 7, a display device 10, and an inspection container 110. Water 15 is accommodated in the inspection container 110, in which the ultrasonic transducer 9, and a semiconductor chip 11, a wiring substrate 13, and connection solders 12, which are inspection objects (ultrasonic wave inspection objects) (hereinafter, the semiconductor chip 11, the wiring substrate 13, and the connection solders 12 are comprehensively referred to as "semiconductor chip 11 and so on") are arranged, being immersed in the water 15.

The ultrasonic transducer 9 is so structured that a plurality of piezoelectric elements 41a, 42a, 43a, . . . , 49a, 50a, 50b, . . . , 50h, each including a piezoelectric material, are arranged in a matrix therein, and the driven element selecting section 2 selects and determines a piezoelectric element to be driven among the piezoelectric elements 41a and the like so that a drive signal from the signal generating section 1 is led thereto through a conductor. Electrical signals generated by the respective piezoelectric elements 41a and the like are led to the signal detecting circuit 4 through conductors. When the piezoelectric elements 41a or the like is electrically driven, an ultrasonic wave is generated due to the nature as the piezoelectric material, and the generated ultrasonic wave reaches the semiconductor chip 111 via the water 15. Echoes of the ultrasonic wave reflected on the semiconductor chip 11 and so on are inputted again to the piezoelectric elements 41a and the like via the water 15 so that each of the piezoelectric elements 41a and the like generates an electrical signal.

The signal generating section 1 generates pulsed or continuous drive signals in order to cause the piezoelectric elements 41a and the like to generate the ultrasonic waves. The generated drive signals are led to the driven element selecting section 2. The driven element selecting section 2 selects one or plural ones of the piezoelectric elements 41a and the like to be driven, and thereafter, leads the drive signals led from the signal generating section 1 to the selected piezoelectric elements 41a and the like.

The signal detecting circuit 4 detects the electrical signals generated in the piezoelectric elements 41 and the like. The plural electrical signals necessary for inspection among the detected electrical signals are led to the amplifiers 5a, 5b, . . . , 5i respectively.

The amplifier 5a, 5b, . . . 5i amplify the led electrical signals to supply them to the A/D converters 6a, 6b, . . . , 6i. The A/D converters 6a, 6b, . . . , 6i A/D-convert the led electrical signals to lead them to the signal processing section 7.

The signal processing section 7 processes the digital signals led from the A/D converters 6a, 6b, . . . , 6i to generate information for visualizing the state of the inspection object. The generated information is led to the display device 10. The display device 10 displays the led information.

The inspection container 110 is a container allowing the semiconductor chips 11 and so on as the inspection objects and the ultrasonic transducer 9 to be immersed in the water 15.

Figure 2:
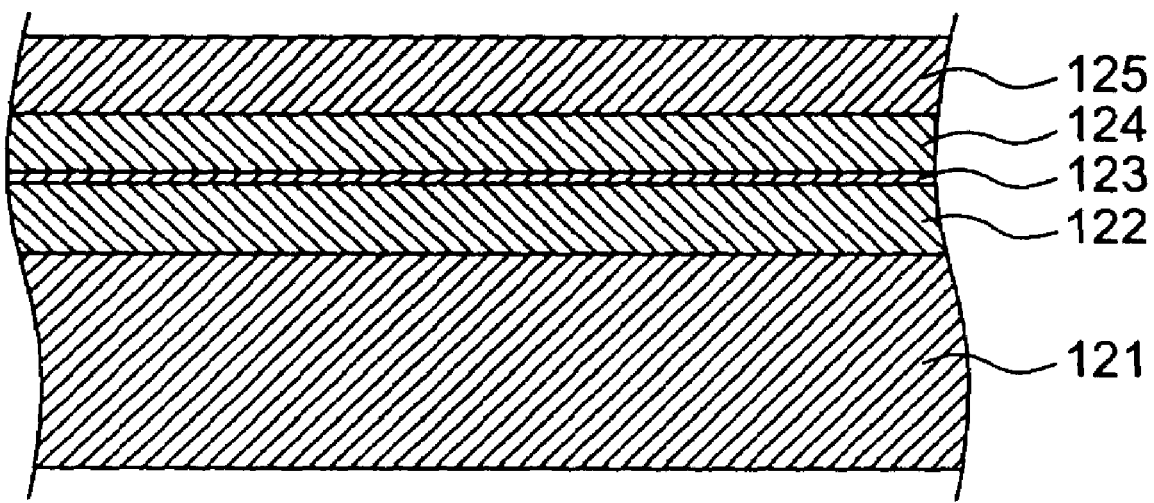
FIG. 2 is a view showing a sectional structure of a piezoelectric element 41a and so on shown in FIG. 1.

FIG. 2 is a diagram showing a cross sectional structure of each of the piezoelectric elements 41a and the like. As shown in this drawing, each of the piezoelectric elements 41a and the like has a ground electrode 122, a surface compound layer 123, a piezoelectric layer 124, and an upper electrode layer 125 from the bottom on a substrate 121. Among them, at least the substrate 121 and the ground electrode 122 are provided in common in all the piezoelectric elements 41a and the like. Usable for the substrate 121 are, for example, monocrystalline or polycrystalline silicon, epoxy, ceramic, and metal such as SUS. The piezoelectric elements 41a and the like as shown in FIG. 2 can be formed by appropriate selection from the methods previously explained.

The inspection operation of the ultrasonograph shown in FIG. 1 will be explained. The signal generating section 1 generates the signal for driving the piezoelectric element 41a and the like, and this signal is led to the piezoelectric element selected by the driven element selecting section 2 (piezoelectric element 46a in the drawing). Triggered by this, the piezoelectric element 46a generates an ultrasonic wave U, and the semiconductor chip 11 and so on are irradiated with the generated ultrasonic wave via the water 15 as a propagation medium.

The ultrasonic wave U with which the semiconductor chip 11 and so on are transmitted is refracted on a surface of the semiconductor chip 11 and further advances to be reflected on, for example, the connection solder 12 where a flaw 14 exists, so that the ultrasonic wave U turns to echoes, which then reach the piezoelectric elements 46a and the like again via the semiconductor chip 11 and the water 15.

As a result, the piezoelectric elements 41a and the like generate the electrical signals. The generated electrical signals are led to the signal detecting circuit 4 and detected therein. In the signal detecting circuit 4, the electrical signals necessary for the inspection (in the drawing, those generated by the piezoelectric elements 41a, . . . , 50a) among the detected electrical signals are led to the amplifiers 5a, . . . , 5i respectively. The amplifiers 5a, . . . , 5i amplify the led signals respectively to supply them to the A/D converters 6a, . . . , 6i.

Further, the signals A/D-converted in the A/D converters 6a, . . . , 6i are taken into the signal processing section 7.

The signal processing section 7 takes signals from the A/D converters 6a, . . . , 6i therein every time the driven element selecting section 2 and the signal detecting circuit 4 perform switching operations, and performs processing for imaging an intensity distribution state of the reflected echoes from a bonding interface between the semiconductor chip 11 and the connection solder 12. The result is displayed on the display device 10. Incidentally, since a reflection intensity of the ultrasonic wave U is increased when the connection solder 12 has the flaw (solder peel-off or the like) 14, the position and degree thereof are known from the processing result of the signal processing section 7.

In this embodiment, the characteristics of the structure and the material of the piezoelectric elements 41a and the like allow high-frequency drive to enable high-resolution inspection, and in addition, since the piezoelectric elements 41a and the like are arranged in a matrix, efficient inspection is made possible compared with mechanical scan of a piezoelectric element.

Incidentally, in this embodiment, the acoustic medium, which is the water 15, is made of different substance from that of the semiconductor chip 11 and so on as the inspection objects. This causes refraction of the ultrasonic wave on the surface of the semiconductor chip 11. Therefore, the signal processing section 7 specifies the route of the ultrasonic wave in the semiconductor chip 11 in consideration of this refraction.

SECOND EMBODIMENT

Figure 3:
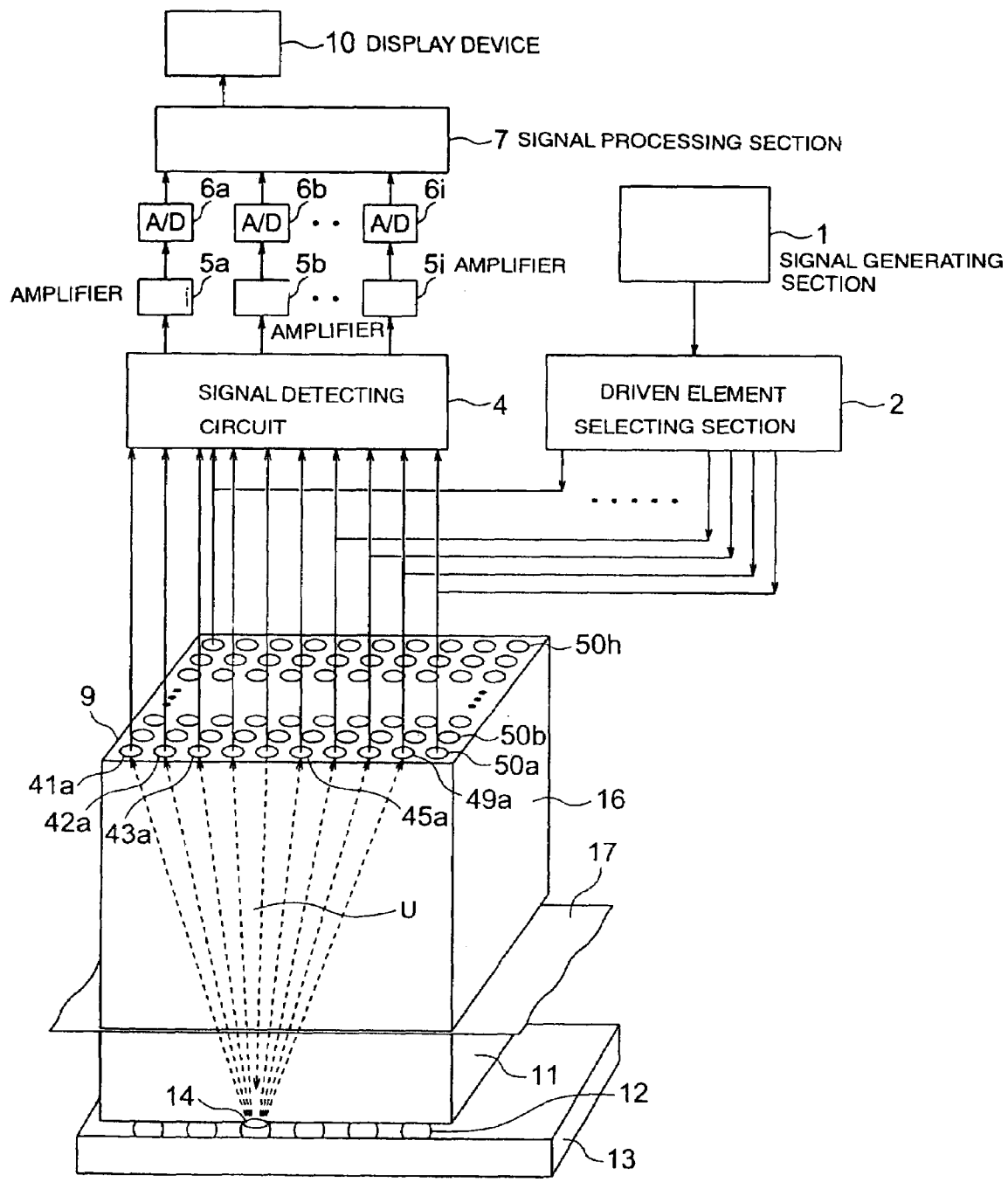
FIG. 3 is a block diagram explaining the configuration of an ultrasonograph according to a second embodiment of the present invention.

FIG. 3 is a block diagram explaining the configuration of an ultrasonograph according to a second embodiment of the present invention. In this drawing, the same numerals are assigned to the constituent elements which are previously explained, and explanation on the structure and operation thereof will be omitted. In this embodiment, unlike the above-described first embodiment, inspection objects are irradiated with an ultrasonic wave not via water but through the use of a shoe member.

As shown in this drawing, an ultrasonic transducer 9 is constituted with a shoe member 16 as a substrate. The shoe member 16 has a couplant 17 provided on a rear face thereof, and is pressed against a semiconductor chip 11 and so on as inspection objects via the couplant 17. The shoe member 16 is made of the same material (for example, silicon, epoxy, ceramic, or the like) as that of the semiconductor chip 11. The couplant 17 can be formed of the same material and to have the same thickness as explained previously, and a sheet-type one as shown in the drawing is used here as an example.

The couplant 17 allows the shoe member 16 and the semiconductor chip 11 and so on to be in contact in a flat state so that ultrasonic waves generated by piezoelectric elements 41a and the like of the ultrasonic transducer 9 advance with almost no refraction on a surface of the semiconductor chip 11, as shown in the drawing. Accordingly, processing in a signal processing section 7 does not require the consideration of the refraction to further facilitate the processing.

Further, it is not necessary to prepare an inspection container to accommodate water therein and the inspection objects are not immersed in the water so that the objects are usable normally even after the inspection. Therefore, besides the sampling inspection, this ultrasonic inspection in the air can be utilized easily.

Also in this embodiment, the characteristics of the structure and the material of the piezoelectric elements 41a and the like allow high-frequency drive to enable high-resolution inspection, and in addition, since the piezoelectric elements 41a and the like are arranged in a matrix, efficient inspection is possible compared with mechanical scan of a piezoelectric element.

THIRD EMBODIMENT

Figure 4:
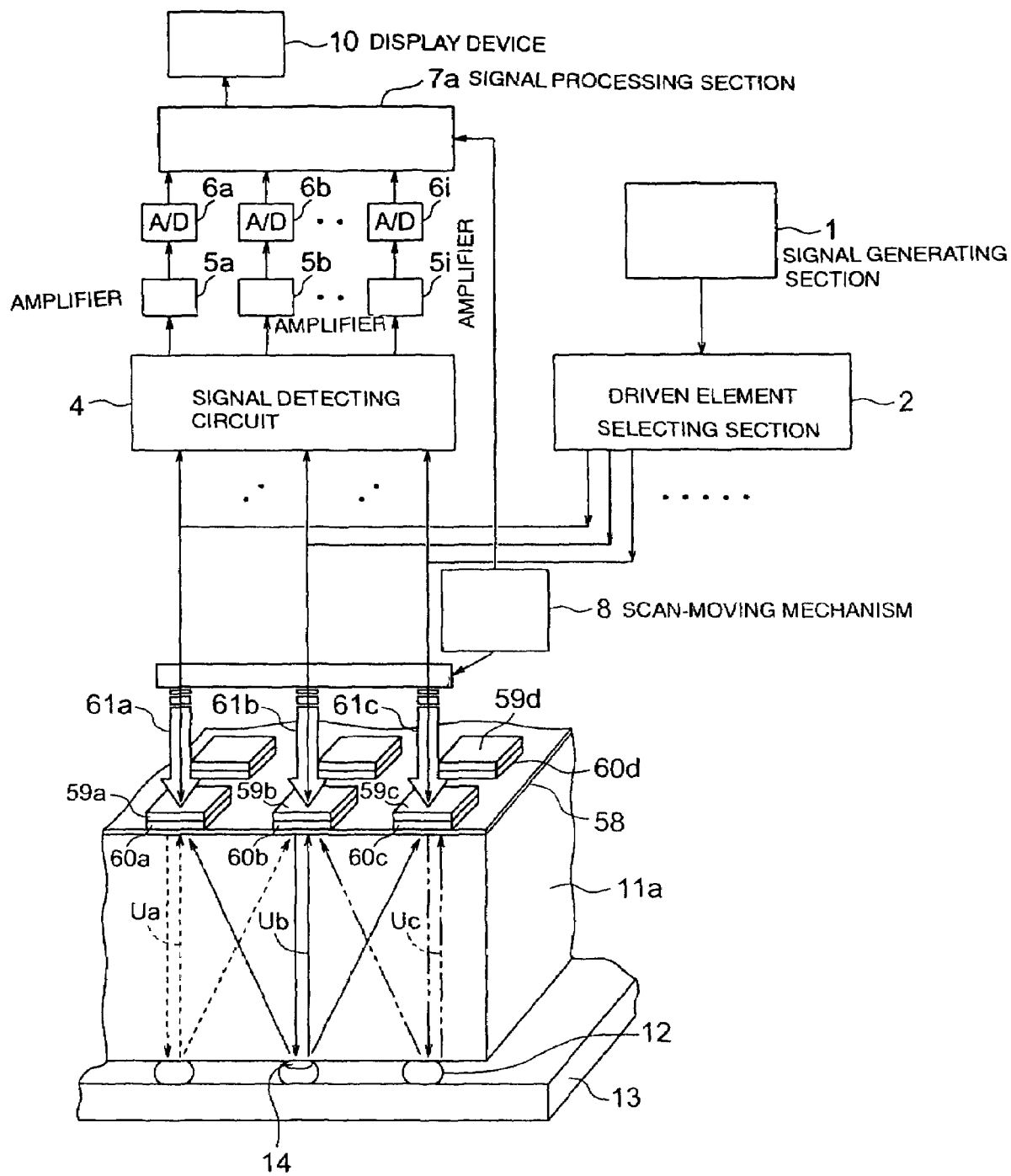
FIG. 4 is a block diagram explaining the configuration of an ultrasonograph according to a third embodiment of the present invention.

FIG. 4 is a block diagram explaining the configuration of an ultrasonograph according to a third embodiment of the present invention. In this drawing, the same numerals are assigned to the constituent elements previously explained and explanation on the structure and operation thereof will be omitted. In this embodiment, piezoelectric elements are formed directly on a rear surface (opposite side of a functional surface) of a semiconductor chip 11a and so on as inspection objects, and contact terminals are brought into contact with upper electrodes thereof to supply drive voltages and take out generated voltages.

As shown in FIG. 4, a common electrode 58 is formed on the rear surface of the semiconductor chip 11a by, for example, sputtering, and piezoelectric layers 60a, 60b, 60c, 60d, . . . are further formed on the common electrode 58 in a matrix. Upper electrodes 59a, 59b, 59c, 59d, . . . are formed on the piezoelectric layers 60a and so on respectively. The piezoelectric layers 60a and so on can be formed by, for example, sputtering using a mask pattern. Incidentally, each of the piezoelectric elements may be arranged and formed so as to correspond to the arrangement of each of connection solders 12 in order to simplify signal processing.

The supply of the drive voltage via the upper electrode 59a and taking-out of the generated voltage are performed by contact terminals 61a, 61b, 61c. The contact terminals 61a and so on can be scan-moved by a scan-moving mechanism 8. Incidentally, three contact terminals are provided in this drawing, but the number thereof may be set as necessary. As the contact terminals 61a and so on, those previously explained are usable in concrete.

A signal processing section 7a obtains as information positions given to the contact terminals 61a and so on by the scan-moving mechanism 8, and based on this information and information from detection signals given by ultrasonic waves Ua, Ub, Uc, and so on, it performs processing for imaging an intensity distribution state of reflected echoes from a bonding interface between the semiconductor chip 11a and the connection solder 12.

In this embodiment, it is not necessary, either, to prepare an inspection container to accommodate water therein and the inspection objects are not immersed in the water so that the objects are usable normally even after the inspection. Therefore, besides the sampling inspection, this ultrasonic inspection in the air can be utilized easily.

Similarly, the characteristics of the structure and the material of the piezoelectric elements allow high-frequency drive to enable high-resolution inspection. Incidentally, the method of supplying the drive voltages and taking out the generated voltages through the use of contact with the piezoelectric elements by the contact terminals 61a and so on, which is explained here, can be utilized in the first and second embodiments in place of connection with the piezoelectric elements 41a and the like, which uses the conductors in the explanation thereof.

FOURTH EMBODIMENT

Figure 5:
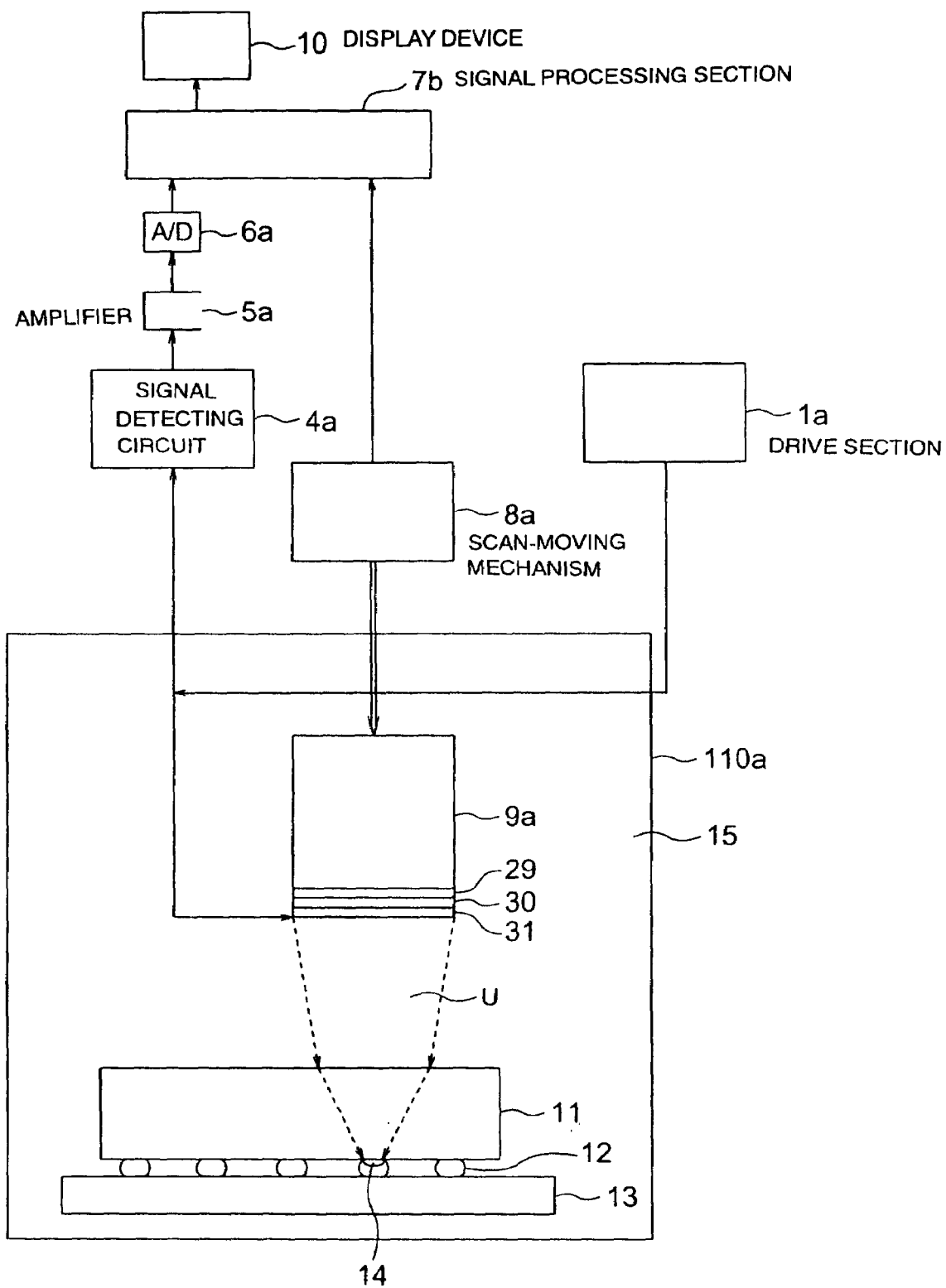
FIG. 5 is a block diagram explaining the configuration of an ultrasonograph according to a fourth embodiment of the present invention.

FIG. 5 is a block diagram explaining the configuration of an ultrasonograph according to a fourth embodiment of the present invention. In this drawing, the same numerals are assigned to the constituent elements previously explained and explanation on the structure and operation thereof will be omitted. In this embodiment, inspection is performed by mechanically scan-moving an ultrasonic transducer.

As shown in this drawing, this ultrasonograph has an ultrasonic transducer 9a, a signal generating circuit 1a, a signal detecting circuit 4a, an amplifier 5a, an A/D converter 6a, a signal processing section 7b, a display device 10, and an inspection container 110a. Water 15 is accommodated in the inspection container 110a, and the ultrasonic transducer 9a, and a semiconductor chip 11 and so on as inspection objects (ultrasonic wave irradiation objects) are disposed therein, being immersed in this water 15.

The ultrasonic transducer 9a is so structured that an electrode layer 29, a piezoelectric layer 30, and an upper electrode layer 31 are layered in sequence on a surface of a substrate having a dished shape, and this layered structure functions as a piezoelectric element. A drive signal from the signal generating circuit 1a is led to the piezoelectric element via a conductor. An electrical signal generated by the piezoelectric element is led to the signal detecting circuit 4a via a conductor. When the piezoelectric element is electrically driven, an ultrasonic wave U is generated due to the nature as the piezoelectric material, and the generated ultrasonic wave reaches the semiconductor chip 11 via the water 15. An echo of the ultrasonic wave caused by the semiconductor chip 11 and so on is inputted to the piezoelectric element again via the water 15, and based on the echo, the piezoelectric element generates the electrical signal.

The signal generating circuit 1a generates a pulsed or continuous drive signal in order to cause the piezoelectric section to generate the ultrasonic wave. The signal detecting circuit 4a detects the electrical signal generated by the piezoelectric element. The detected electrical signal is led to the amplifier 5a. The subsequent A/D converter 6a and the display device 10 are the same as those explained previously.

The signal processing section 7b obtains as information and processes the digital signal led from the A/D converter 6a and a position given to the ultrasonic transducer 9a by the scan-moving mechanism 8a, to thereby generate information for visualizing a state of the inspection objects. The generated information is led to the display device 10.

The scan-moving mechanism 8a is provided as a mechanism which sets the position of the ultrasonic transducer 9a, and the information on the position to be set is led to the signal processing section 7b. The inspection container 110a is a container in which the semiconductor chip 11 and so on as the inspection objects and the ultrasonic transducer 9a are to be immersed in the water 15.

To further explain the layered structure of the ultrasonic transducer 9a, the electrode layer 29 can be formed so as to function as an adhesive layer as well which utilizes electrostatic attraction. A material thereof can be selected from Cr, Ta, Si, and so on. The piezoelectric layer 30 can be formed in such manner that the material as explained previously is processed into a thin film by polishing to have a thickness of, for example, about 10 µm and this thin film is made to adhere. Incidentally, when a conductive material (for example, doped Si monocrystal or the one with only a surface layer thereof doped) is used as the substrate under the electrode layer 29 in the drawing, the electrode layer 29 need not be formed.

The inspection operation of the ultrasonograph shown in FIG. 5 will be explained. The scan-moving mechanism 8a determines the position of the ultrasonic transducer 9a, and the signal for driving the ultrasonic transducer 9a is generated in the signal generating circuit 1a. Triggered by this, the ultrasonic transducer 9a generates the ultrasonic wave U, and the semiconductor chip 11 and so on are irradiated with the generated ultrasonic wave via the water 15 as a propagation medium.

The ultrasonic wave U with which the semiconductor chip 11 and so on are irradiated is refracted on a surface of the semiconductor chip 11 to further advance, and is reflected on, for example, a connection solder 12 where a flaw 14 exists, to turn to an echo so that the echo reaches the ultrasonic transducer 9a again via the semiconductor chip 11 and the water 15.

As a result, the ultrasonic transducer 9a generates the electrical signal. The generated electrical signal is led to the signal detecting circuit 4a to be detected therein. The signal detecting circuit 4a leads the detected electrical signal to the amplifier 5a. The amplifier 5a amplifies the led signal to supply this signal to the A/D converter 6a. Further, the signal A/D-converted in the A/D converter 6a is taken into the signal processing section 7b.

The signal processing section 7b obtains as information and processes the digital signal led from the A/D converter 6a and the position given to the ultrasonic transducer 9a by the scan-moving mechanism 8a, and performs processing for imaging an intensity distribution state of the reflected echoes from a bonding interface between the semiconductor chip 11 and the connection solder 12. The result thereof is displayed on the display device 10. Such processing can be performed every time the scan-moving mechanism 8a determines the position of the ultrasonic transducer 9a.

In this embodiment, the characteristics of the structure and the material of the ultrasonic transducer 9a allow high-frequency drive to enable higher resolution inspection. Further, the adhesion utilizing, for example, electrostatic force makes it possible to form the piezoelectric layer 30 more uniformly on the substrate so that deterioration of sensitivity and resolution due to low uniformity can be prevented.

Incidentally, also in this embodiment, an acoustic medium is the water 15, which is made of different substance from that of the semiconductor chip 11 and so on as the inspection objects, so that the ultrasonic wave U is refracted on the surface of the semiconductor chip 11. So, the signal processing section 7b specifies a route of the ultrasonic wave in the semiconductor chip 11 in consideration of this refraction.

FIFTH EMBODIMENT

Figure 6:
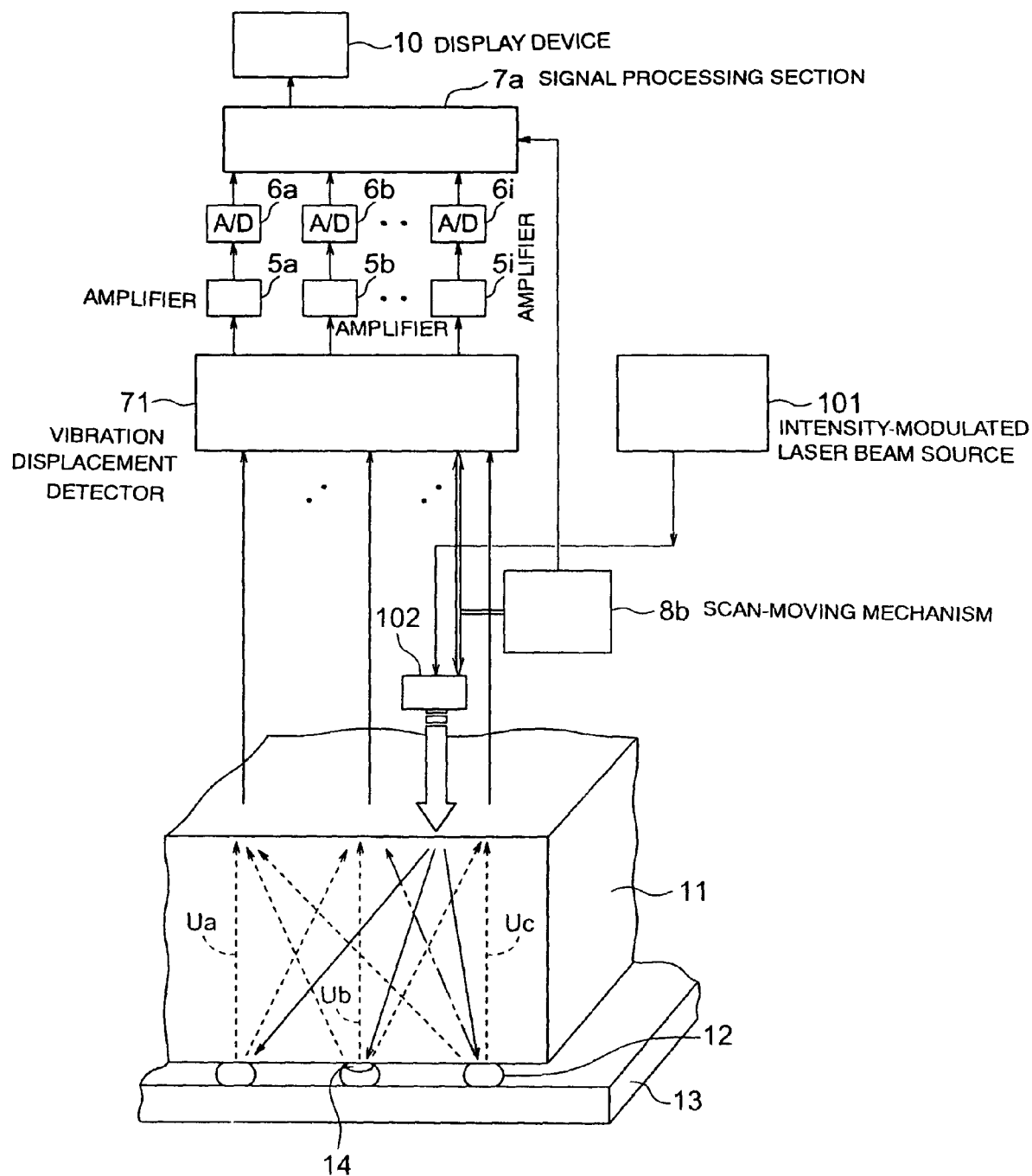
FIG. 6 is a block diagram explaining the configuration of an ultrasonograph according to a fifth embodiment of the present invention.

FIG. 6 is a block diagram explaining the configuration of an ultrasonograph according to a fifth embodiment of the present invention. In this drawing, the same numerals will be assigned to the constituent elements previously explained, and explanation on the structure and operation thereof will be omitted. In this embodiment, a laser beam is used to cause inspection objects to generate ultrasonic waves, and echoes thereof are detected and processed to inspect the inspection objects.

As shown in this drawing, this ultrasonograph has an intensity-modulated laser beam source 101, an optical transmitter 102, a vibration displacement detector 71, amplifiers 5a, 5b, . . . , 5i, A/D converters 6a, 6b, . . . , 6i, a signal processing section 7, a display device 10, and a scan-moving mechanism 8b. A semiconductor chip 11 and so on as inspection objects are irradiated with a laser beam from the optical transmitter 102 whose position is determined by the scan-moving mechanism 8b.

The intensity-modulated laser beam source 101 generates an intensity-modulated laser beam (it may be an intermittent laser beam as a peculiar case of intensity modulation), and the generated laser beam is led to the optical transmitter 102. The optical transmitter 102 irradiates a predetermined position of the semiconductor chip 11 as the inspection object with the led laser beam in a spot-like state. For achieving the irradiation on the predetermined position, the optical transmitter 102 is scan-moved by the scan-moving mechanism 8b. Incidentally, the irradiation of the laser beam causes energy conversion in the semiconductor chip 11 so that ultrasonic waves are generated.

The vibration displacement detector 71 conducts non-contact detection of the ultrasonic waves returning from each part to a surface of the semiconductor chip 11 as echoes to convert them to electrical signals. The detection principle is such that the vibration displacement detector 71 detects and measures vibration displacement which occurs on the surface of the semiconductor chip 11 due to the ultrasonic waves returning to the surface thereof, based on phase change of the irradiated and reflected laser beam. The plural electrical signals necessary for the inspection among the detected electrical signals are led to the amplifiers 5a, 5b, . . . , 5i respectively. The A/D converters 6a, 6b, . . . , 6i, the signal processing section 7, and the display device 10 as subsequent configuration are the same as those explained previously.

The scan-moving mechanism 8b moves the optical transmitter 102 and the vibration displacement detector 71 synchronously, and, at the same time, supplies the signal processing section 7a with position information on the optical transmitter 102 and the vibration displacement detector 71.

The inspection operation of the ultrasonograph shown in FIG. 6 will be explained. The laser beam generated in the intensity-modulated laser beam source 101 is led to the optical transmitter 102, and the optical transmitter 102 irradiates the predetermined position of the semiconductor chip 11 as the inspection object with the led laser beam in a spot-like state. Note that this position is set by the scan-moving mechanism 8b. As a result, the ultrasonic waves are generated from the surface of the semiconductor chip II at this position.

The ultrasonic waves generated on the surface of the semiconductor chip 11 advance inside the semiconductor chip 11 to be reflected on, for example, a connection solder 12 where a flaw 14 occurs so that they turn to echoes Ua, Ub, Uc to reach the surface of the semiconductor chip 11 again.

As a result, the vibration displacement detector 71 generates, based on the above principle, the plural electrical signals corresponding to the ultrasonic waves returning to the respective parts of the surface of the semiconductor chip 11. The electrical signals necessary for the inspection among the generated electrical signals are led to the amplifiers 5a, . . . , 5i respectively. The amplifiers 5a, . . . , 5i amplify the led signals respectively to supply them to the A/D converters 6a, . . . , 6i. Further, the signals A/D-converted in the A/D converters 6a, . . . , 6i are taken into the signal processing section 7a.

The signal processing section 7a obtains as information the positions given to the optical transmitter 102 and so on by the scan-moving mechanism 8b, and based on this information and the aforesaid signals taken therein, performs processing for imaging an intensity distribution state of the reflected echoes from a bonding interface between the semiconductor chip 11 and the connection solder 12.

In this embodiment, the laser beam generated intermittently or with intensity modulation is made in a spotted state so that an ultrasonic wave generating source with an extremely small area can be formed at an accurate position on the inspection object. In this way, high-resolution detection is made possible by catching the echoes.

Further, since it is not necessary to prepare an inspection container to accommodate water therein and the inspection objects are not immersed in the water, the objects are normally usable even after the inspection. Therefore, besides the sampling inspection, this ultrasonic inspection in the air can be easily utilized.

SIXTH EMBODIMENT

Next, an ultrasonic imaging device according to an embodiment of the present invention will be explained with reference to the drawings.

Figure 7:
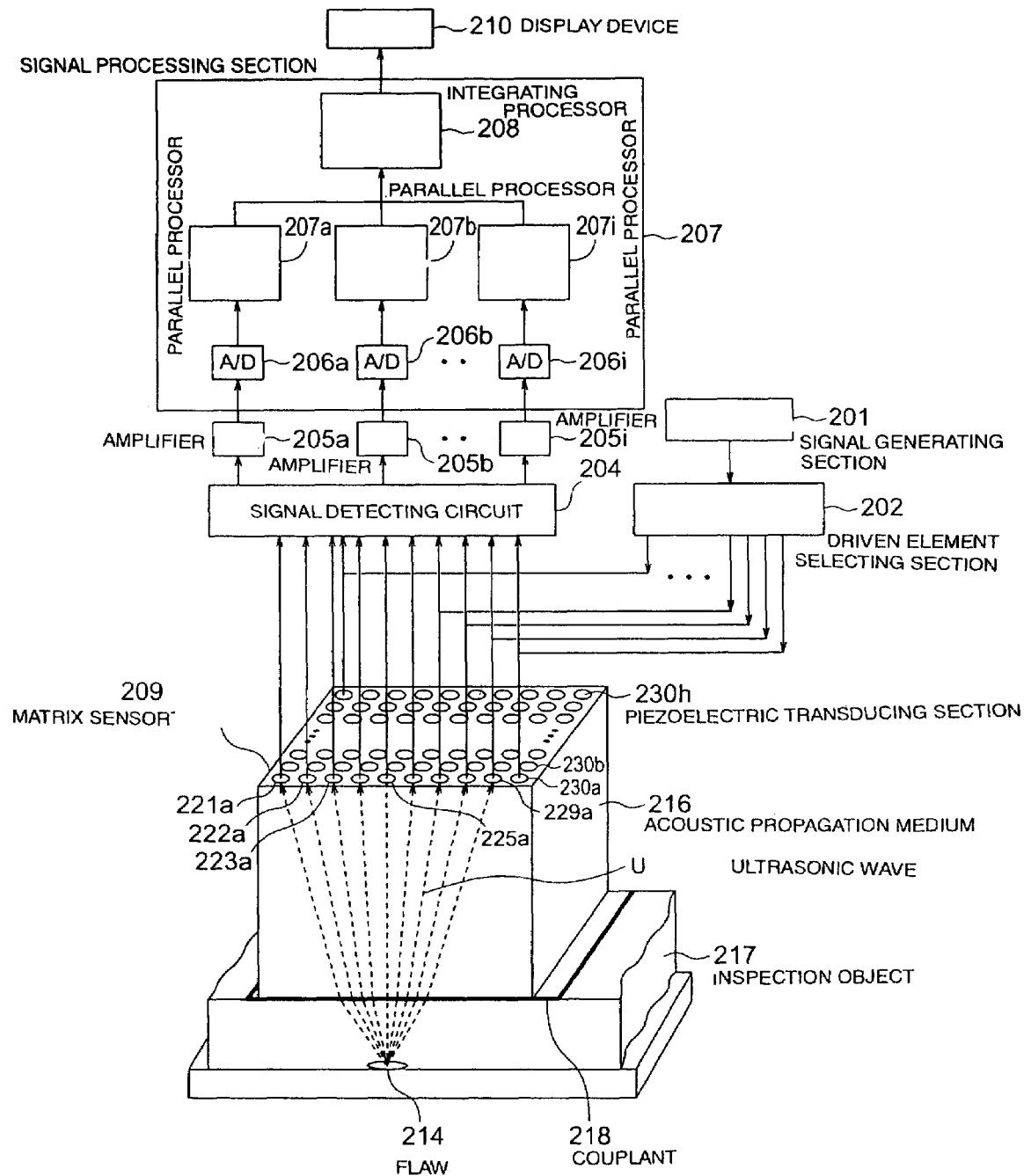
FIG. 7 is a diagram explaining a configuration example when ultrasonic inspection is conducted by an ultrasonic imaging device according to a sixth embodiment of the present invention.

FIG. 7 is a diagram explaining a configuration example when ultrasonic inspection is conducted by the ultrasonic imaging device according to the embodiment of the present invention. As shown in this drawing, this ultrasonic imaging device has an array transducer (ultrasonic transducer) 209, a signal generating section 201, a driven element selecting section 202, a signal detecting circuit 204, amplifiers 205a, 205b, ..., 205i, a signal processing section 270, and a display device 210. The above signal processing section 270 has as an internal configuration thereof A/D converters 206a, 206b, ..., 206i, parallel processors 207a, 207b, ..., 207i, and an integrating processor 208. An acoustic propagation medium 216 is in close contact with a front face of the array transducer 209, and the acoustic propagation medium 216 is in contact with an inspection object 217 via a couplant 218. A flaw 214 may possibly exist in the inspection object 217.

The array transducer 209 is so structured that a plurality of piezoelectric elements 221a, 222a, 223a, ..., 229a, 230a, 230b, ..., 230h, each made of a piezoelectric element, are arranged in a matrix, and after those to be driven among the piezoelectric elements 221a and so on are determined by the selection by the driven element selecting section 202, drive signals from the signal generating section 201 are led thereto through conductors. Electrical signals generated by the respective piezoelectric elements 221a and so on are led to the signal detecting circuit 204 through conductors. When the piezoelectric elements 221a and so on are electrically driven, ultrasonic waves are generated due to the nature as piezoelectric materials, and the generated ultrasonic waves reach the flaw 214 inside the inspection object 217 via the acoustic propagation medium 216. Ultrasonic wave echoes U caused by the flaw 214 are inputted again to the piezoelectric elements 221a and so on via the acoustic propagation medium 216, and as a result, the piezoelectric elements 221a and so on generate the electrical signals respectively.

The signal generating section 201 generates the pulsed or continuous drive signals in order to cause the piezoelectric elements 221a and so on to generate the ultrasonic waves. The generated drive signals are led to the driven element selecting section 202. The driven element selecting section 202 selects one or plural ones to be driven from the piezoelectric elements 221a and so on, and leads the drive signals led from the signal generating section 201 to the selected piezoelectric elements 221a and so on.

The signal detecting circuit 204 detects the electrical signals generated by the piezoelectric elements 221a and so on. Plural electrical signals necessary for inspection among the detected electrical signals are led to the amplifiers 205a, 205b, ..., 205i.

The amplifiers 205a, 205b, ..., 205i amplify the led electrical signals respectively and supply them to the A/D converters 206a, 206b, ..., 206i respectively in the signal processing section 270. The A/D converters 206a, 206b, ..., 206i A/D-convert the led electrical signals to lead them to the parallel processors 207a, 207b, ..., 207i in the signal processing section 270 respectively.

The parallel processors 207a, 207b, ..., 207i in the signal processing section 270 process in parallel the digital signals led from the A/D converters 206a, 206b, ..., 206i, and specify reflection intensities from each mesh in an area to be imaged. The specified reflection intensities are integrated by the integrating processor 208 to turn to imaged information, which is further led to the display device 210. The display device 210 displays the led information thereon.

Figure 8:
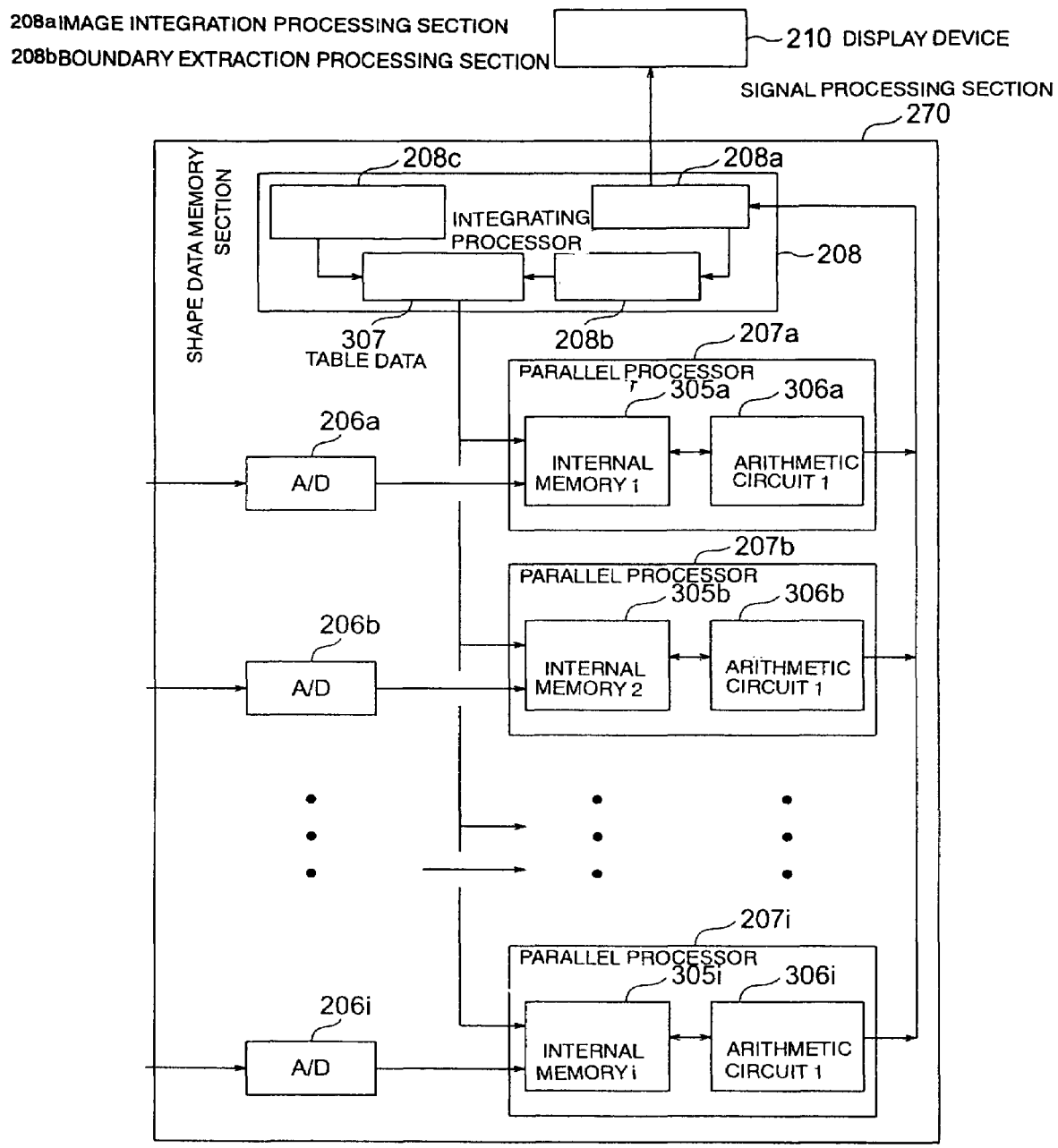
FIG. 8 is a diagram showing in more detail the configuration inside a signal processing section 207 shown in FIG. 7.

FIG. 8 is a diagram showing the configuration inside the signal processing section 270 in more detail. As shown in this drawing, the parallel processors 207a, 207b, ..., 207i have internal memories 305a, 305b, ..., 305i, and arithmetic circuits 306a, 306b, ..., 306i respectively. The integrating processor 208 has an image integration processing section 208a, a boundary extraction processing section 208b, a shape data memory section 208c, a table data storage section 307.

The internal memories 305a, 305b, ..., 305i temporarily store the A/D-converted signals supplied from the A/D converters 206a, 206b, ..., 206i and propagation time data obtained from the table data storage section 307 respectively. The arithmetic circuits 306a, 306b, ..., 306i specify the reflection intensities from each mesh in the area to be imaged based on the A/D-converted signals and the propagation time data stored in the internal memories 305a, 305b, ..., 305i respectively to relate the reflection intensities with each mesh. The related reflection intensities are supplied to the image integration processing section 208a.

The image integration processing section 208a adds the supplied reflection intensities for each mesh to generate the imaged information. The generated imaged information is led to the display device 210.

The boundary extraction processing section 208b extracts a boundary existing inside the inspection object from the result outputted by the image integration processing section 208a. Information on the extracted boundary is sent to the table data storage section 307.

The shape data memory section 208c stores in advance information on a surface shape and a layered structure regarding the inspection object 217. The stored information is sent to the table data storage section 307 when necessary.

The table data storage section 307 tabularizes ultrasonic wave propagation time between the piezoelectric elements 221a and so on (alternatively, it may be equivalent distance. The same applies hereafter.) to store the ultrasonic wave propagation time in advance. A part or all of the stored ultrasonic wave propagation time is transferred to the internal memories 305a, 305b, ..., 305i in the parallel processors 207a, 207b, ..., 207i when necessary. The ultrasonic wave propagation time stored in the table data storage section 307 can be reset based on the information on the extracted boundary in the inspection object, which is supplied by the boundary extraction processing section 208b, and the information on the surface shape and the layered structure regarding the inspection object 217, which is supplied by the shape data memory section 208c.

Figure 9:
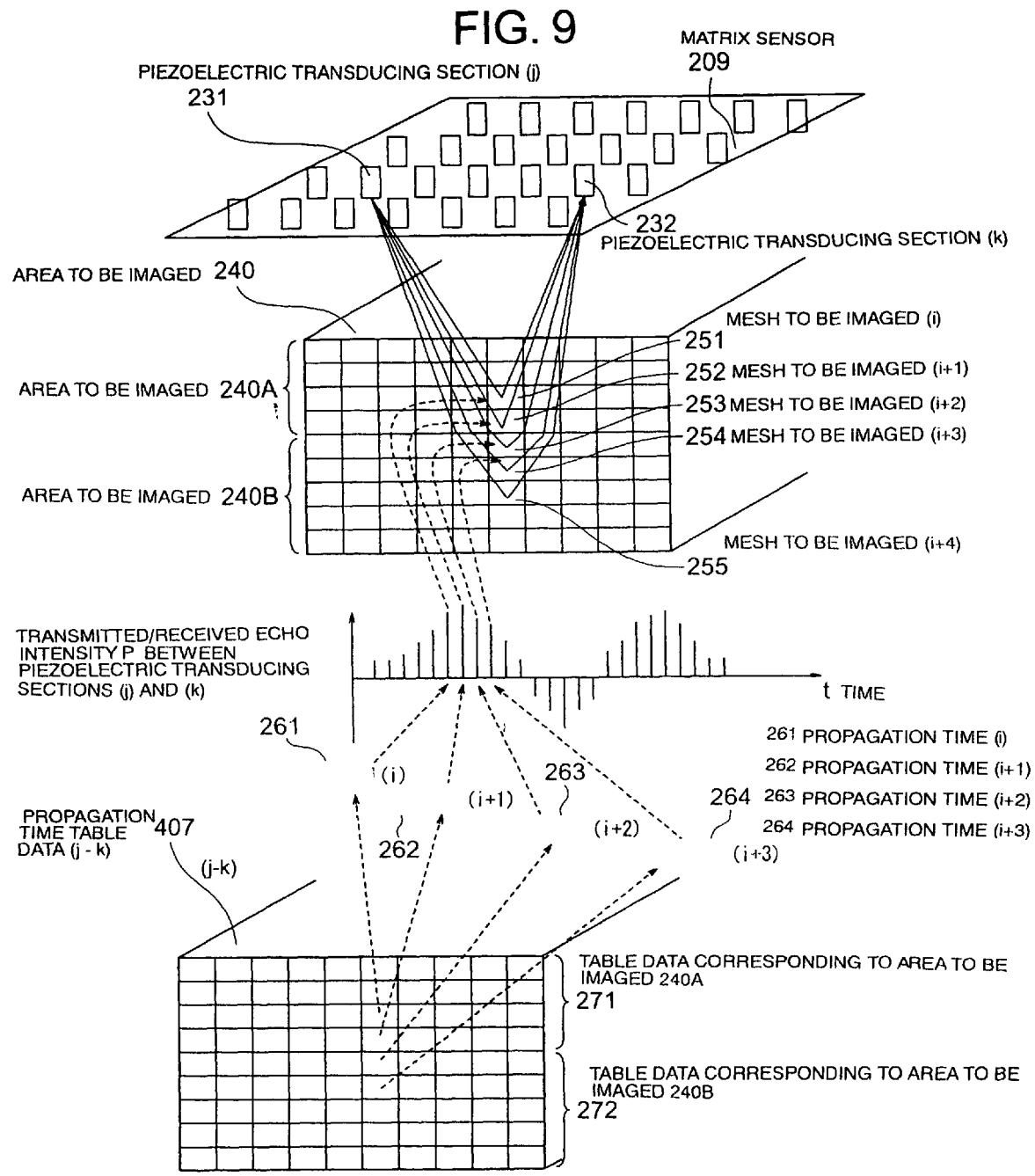
FIG. 9 is an explanatory diagram explaining processing performed inside each of parallel processors 207a, 207b, . . . , 207i shown in FIG. 8.

Next, an example of the actual operation and processing with the configuration shown in FIG. 7 and FIG. 8 will be explained with reference to FIG. 9 as well. FIG. 9 is an explanatory diagram explaining processing performed inside each of the parallel processors 207a, 207b, ..., 207i.

The signal for driving the piezoelectric element 221a or the like is generated in the signal generating section 201, and this signal is led to the piezoelectric element selected by the driven element selecting section 202 (the piezoelectric element 225a in the drawing). Triggered by this, the piezoelectric element 225a generates the ultrasonic wave U, and the inspection object 127 is irradiated with the generated ultrasonic wave via the acoustic propagation medium 216 and the couplant 218.

The ultrasonic wave U with which the inspection object 217 is irradiated is refracted on a surface thereof to further advance so that it is reflected on, for example, the flaw 214 to turn to echoes, which then reach the piezoelectric element 221a and so on again via the inspection object 217.

As a result, the piezoelectric elements 221a and so on generate the electrical signals. The generated electrical signals are led to the signal detecting circuit 204 to be detected therein. The signal detecting circuit 204 leads the electrical signals necessary for the inspection among the detected electrical signals (those generated by the piezoelectric elements 221a, . . . , 229a in the drawing) to the amplifiers 205a, . . . , 205i respectively. The amplifiers 205a, . . . , 205i amplify the led signals respectively to supply them to the A/D converters 206a, . . . , 206i in the signal processing section 270. Further, the signals A/D-converted in the A/D converters 206a, . . . , 206i are supplied to the parallel processors 207a, 207b, . . . , 207i respectively.

Processing in each of the parallel processors 207a, 207b, . . . , 207i is performed in the following manner. Referring to FIG. 9, a piezoelectric element (j) 231 on the array transducer 209 corresponds to the piezoelectric element 225a generating the ultrasonic wave (=transmitting-side) in FIG. 7. A piezoelectric element (k) 232 on the array transducer 209 corresponds to one of the piezoelectric elements 221a, . . . , 229a (receiving-side piezoelectric elements) in FIG. 7.

An area to be imaged 240 corresponds to the acoustic propagation medium 216 and the inspection object 217 in FIG. 7, in which an area to be imaged 240A corresponds to the acoustic propagation medium 216 and an area to be imaged 240B corresponds to the inspection object 217 respectively. The areas to be imaged 240A, 240B are captured, being divided in three-dimensional meshes (or simply, two-dimensional meshes in a visible cross section) as shown in the drawing. Note that the area to be imaged 240A and the array transducer 209 are so depicted as to be apart from each other for the convenience of illustration though they should be so depicted as to be in surface contact with each other as shown in FIG. 7.

A transmitted/received echo intensity P detected by the piezoelectric element (k) 232 and inputted to one of the parallel processors 207a, 207b, . . . , 207i is a time discrete signal as time direction data, for example, as shown about in the middle of FIG. 9. Each of sampled intensities in this time discrete signal is originated from reflection from any one of the meshes in the area to be imaged 240.

Propagation time table data 407 is used for relating the intensities with the meshes. This propagation time table data 407 has been stored in the table data storage section 307 in FIG. 8. The propagation time table data 407 is prepared for each combination (j, k) of the transmitting-side piezoelectric element (j) 231 and the receiving side piezoelectric element (k), and is a table in which propagation time for (j→i→k) corresponding to each mesh in the area to be imaged 240 is recorded. As shown in the drawing, here, it consists of table data 271 corresponding to the area to be imaged 240A and table data 272 corresponding to the area to be imaged 240B. The propagation time table data 407 also has a three-dimensional structure (or simply, a two-dimensional structure of a visible cross section) corresponding to the area to be imaged 240 as shown in the drawing.

Now, when the reflection intensity from, for example, a mesh to be imaged (i) 251 is determined from the data on the transmitted/received echo intensity P, propagation time (i) 261 is first taken out from a storage position, which corresponds to the mesh to be imaged (i) 251, in the propagation time table data 407. Then, a sampling value of the transmitted/received echo intensity P of time t corresponding to the propagation time (i) 261 is specified. This sampling value is the reflection intensity from the mesh to be imaged (i) 251.

In a similar manner, using propagation time (i+1) 262, propagation time (i+2) 263, propagation time (i+3) 264, . . . , the reflection intensities for a mesh to be imaged (i+1) 252, a mesh to be imaged (i+2) 253, a mesh to be imaged (i+3) 254, a mesh to be imaged (i+4) 255, . . . can be also determined.

The determination of the reflection intensities for each of the meshes as described above is carried out by the respective parallel processors 207a, 207b, . . . , 207i in parallel in the signal processing section 270 by varying a value for k of the receiving-side piezoelectric element (k) 232. Then, the results thereof are sent to the image integration processing section 208a to be added for each mesh. In short, in the processing explained above, the parallel processors 207a, 207b, . . . , 207i perform parallel processing so that very high-speed processing is realized.

Note that a final image is obtained, for example, at an instant when the above processing is finished for all the combinations of the transmitting-side piezoelectric element (j) 231 and the receiving-side piezoelectric element (k). For simplification, it may be obtained, for example, at an instant when the above processing is finished for all the combinations of the transmitting-side piezoelectric element (j) 231 and the receiving-side piezoelectric element (k) in one column. The results thereof are displayed on the display device 210. Incidentally, when there exists the flaw 214, the reflection intensity of the ultrasonic wave U from this area is made higher, which means that an imaged result reflects the position and degree thereof.

The propagation time table data 407 can be prepared in advance by performing refraction calculation in consideration of difference in material between the areas to be imaged 240A and 240B to specify a propagation route. Here, the difference in material between the areas to be imaged 240A and 240B causes refraction on the interface therebetween as shown in the drawing, and the propagation time for (j→i→k) is calculated in consideration of this refraction.

The propagation time table data 407 is initially stored in the table data storage section 307 in FIG. 8, but in actual processing, necessary parts are transferred to the internal memories 305a, 305b, . . . , 305i for utilization. The structure of this transfer can contribute to higher-speed processing as a whole, using high-speed memories as the internal memories 305a, 305b, . . . , 305i.

Figure 10:
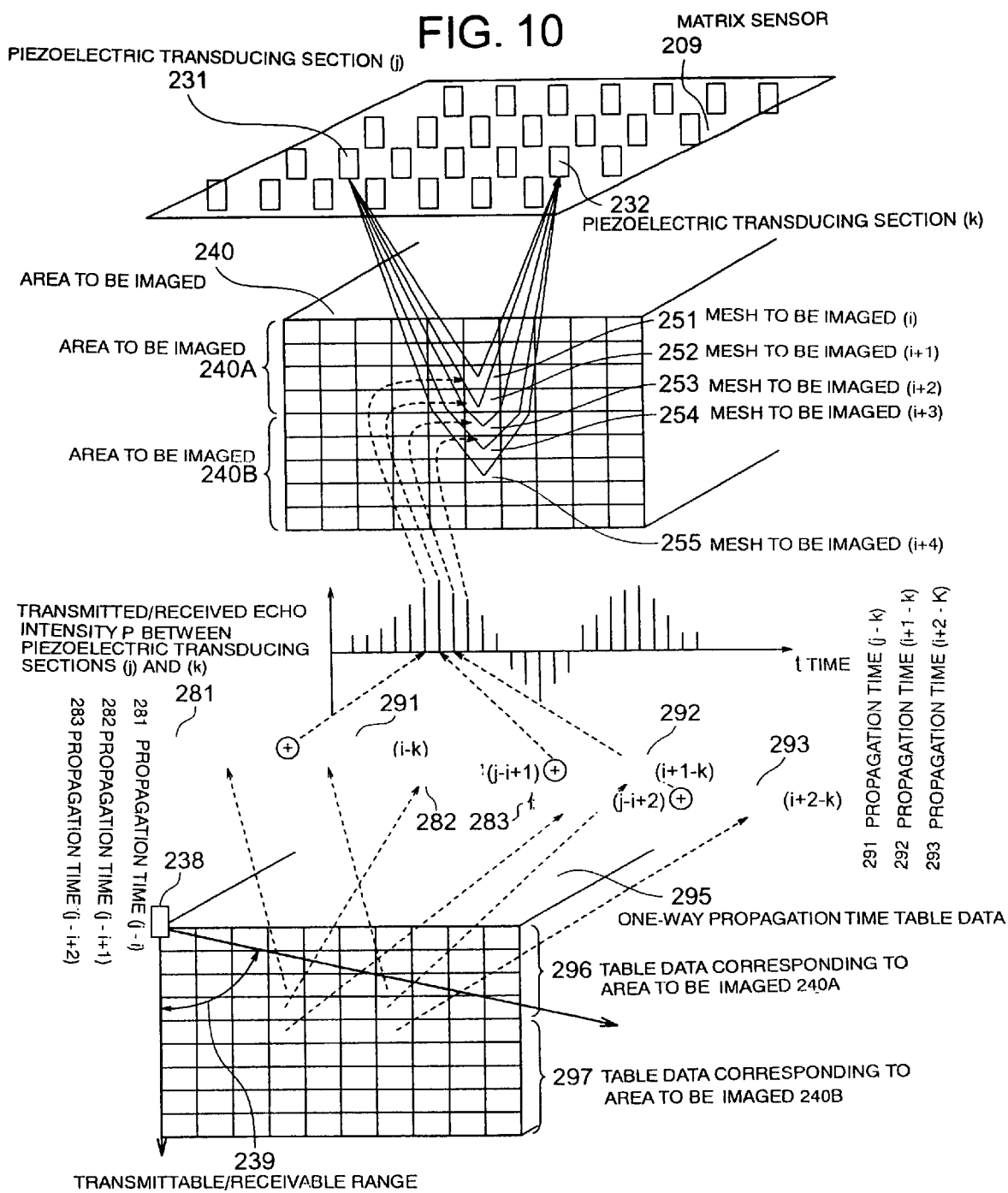
FIG. 10 is an explanatory diagram explaining another example of the processing performed inside each of the parallel processors 207a, 207b, . . . 207i shown in FIG. 8.

Next, another example of the actual operation and processing with the configuration shown in FIG. 7 and FIG. 8 will be explained with reference to FIG. 10 as well. FIG. 10 is an explanatory diagram explaining another example of the processing performed in each of the parallel processors 207a, 207b, . . . , 207i, and the same numerals and symbols are assigned to the portions explained in FIG. 9. Hereinafter, explanation will be given avoiding repeated description.

In this processing example, used is, in place of the propagation time table data 407, one-way propagation time table data 295 which is commonly used, irrespective of the combinations (j, k) of the transmitting-side piezoelectric elements (j) 231 and the receiving-side piezoelectric elements (k) and in which one-way propagation time is stored. The one-way propagation time table data 295 consists of table data 296 corresponding to the area to be imaged 240A and table data 297 corresponding to the area to be imaged 240B.

Even such one-way propagation time table data 295 can be utilized when the inspection object 217 has a symmetric shape and planar surface. This is because uniform propagation time can be assumed for the transmitting-side based on a value for a difference (j−i), in other words, not based on individual values for j. Similarly, for the receiving-side, uniform propagation time can be assumed based on a value for a difference (i−k), in other words, not based on individual values for k.

Now, the reflection intensity from, for example, the mesh to be imaged (i) 251 is to be determined from the data on the transmitted/received echo intensity P, transmitting-side propagation time (j−i) 281 is taken out with (j−i) as an argument from the one-way propagation time table data 295. Similarly, receiving-side propagation time (i−k) 291 is taken out with (i−k) as an argument from the one-way propagation time table data 295. Then, the transmitting-side propagation time (j−i) 281 and the receiving-side propagation time (i−k) 291 are added to specify a sampling value of the transmitted/received echo intensity P of the time t corresponding to the added value. This sampling value is the reflection intensity from the mesh to be imaged (i) 251.

Similarly, the reflection intensities for the mesh to be imaged (i+1) 252, the mesh to be imaged (i+2) 253, the mesh to be imaged (i+3) 254, the mesh to be imaged (i+4) 255, can be determined, using propagation time (j−i+1) 282, propagation time (j−i+2) 283, . . . , and propagation time (i+1−k) 292, propagation time (i+2−k) 293, . . . .

As is explained above, in this example, in place of the propagation time table data 407, used is the one-way propagation time table data 295 which is commonly used, irrespective of the combinations (j, k) of the transmitting-side piezoelectric elements (j) 231 and the receiving-side piezoelectric elements (k) and in which one-way propagation time is stored so that necessary storage areas can be greatly reduced.

Incidentally, the storage areas can be further reduced by taking the following measure. Specifically, since an ultrasonic wave transmitted from a reference piezoelectric element 238 shown in FIG. 10 has directivity, it is not necessary to prepare storage areas corresponding to a range outside a transmittable/receivable range 239. No storage area is provided in such a range. (Note that the reference piezoelectric element 238 is provided at upper left and not at upper center in the drawing because a horizontal symmetric property is utilized.)

Next, several supplementary comments will be given regarding the operation and processing example with the configurations shown in FIG. 7 and FIG. 8.

When the propagation time table data 407 and the one-way propagation time table data 295 are prepared, sensitivity distribution data according to the directivity may be stored in these table data in addition to the propagation time in consideration of the directivity of the piezoelectric elements 221a and so on. In this manner, a gain of an oblique component of an ultrasonic wave whose sensitivity gets low is corrected and echo data of the oblique component can be used so as to contribute to precision improvement.

Further, when the propagation time table data 407 and the one-way propagation time table data 295 are prepared, the table data may be initially set by the integrating processor 208, which is a data supplying means, on assumption that an inspection object is a single layer of an acoustic propagation medium made of a solid or liquid (note that the configuration inside the integrating processor 208 for this purpose is not shown). When results obtained by this processing and setting are imaged, a boundary surface between the acoustic propagation medium 216 and the true inspection object 217 (namely, a discontinuous line or a discontinuous surface) can be extracted and detected (the processing is performed in the boundary extraction processing section 208b). This is because the existence and the position of the boundary surface can be specified since the assumed result and the actual result differ according to the position where the boundary surface exists.

Then, when the integrating processor 208 resets each of the table data 407, 295 described above based on this specifying of the boundary surface (note that the configuration inside the integrating processor 208 for this purpose is not shown), and each of the reset table data 407, 295 is used, it is possible to cope with imaging in the case when the position and the shape of the inspection object 217 shifts.

Further, in case the true inspection object 217 has a complicated shape, shape data may be stored in the shape data memory section 208c in advance and an operation may be performed so as to reset the propagation time table data 407 and the one-way propagation time table data 295 in consideration of this stored shape data.

SEVENTH EMBODIMENT

Next, an ultrasonograph according to another embodiment of the present invention will be explained with reference to the drawing.

Figure 11:
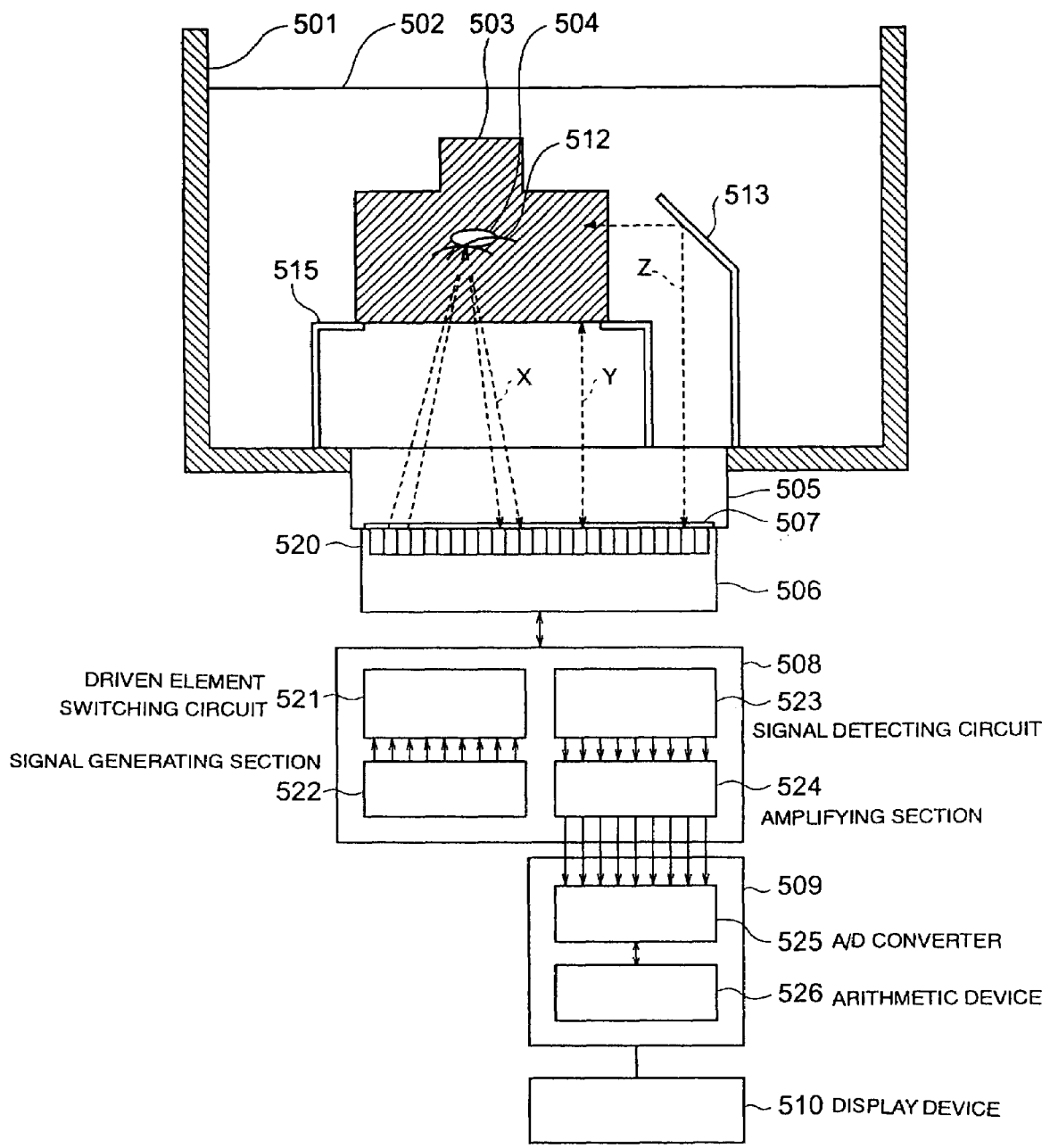
FIG. 11 is a schematic diagram showing an ultrasonograph according to a seventh embodiment of the present invention.

FIG. 11 is a schematic diagram explaining the configuration of an ultrasonograph according to a seventh embodiment of the present invention. As shown in this drawing, this ultrasonograph has an array transducer 506 which is an ultrasonic transducer composed of many piezoelectric elements arranged in a matrix or in a line, a transmission/reception switching device 508, an image synthesizing device 509, and a display device 510, and it can visualize and display a flaw 504 inside an object 503 to be inspected immersed in water 502 in a container 501. A shoe member 505 in a flat plate shape is fixedly in close contact with a front face of the array transducer 506 via a couplant 507. Moreover, a reflector 513 and a fixing stand 515 are provided in the container 501.

The container 501 is a container in which the water 502 and the object 503 to be inspected are accommodated and is intended for use in inspecting the object 503 to be inspected by an ultrasonic wave while it is immersed in the water 502.

The water 502 is a kind of a liquid acoustic medium which propagates ultrasonic waves. This means that liquid other than the water 502, for example, oil or the like is usable as the liquid acoustic medium.

The object 503 to be inspected is an inspection object for which the inspection of the existence or nonexistence of a flaw 504 (for example, a void, peel-off of coupling, and so on) is carried out through inner state inspection by ultrasonic waves. Note that the fixing stand 515 determines the position of the object 503 to be inspected and fixes it in the container 501.

The shoe member 505, which is an acoustic medium (solid acoustic medium) made of a flat plate solid, serves as a part of a propagation route of the ultrasonic wave between the array transducer 506 and the object 503 to be inspected, and can be constituted of an appropriate material such as, for example, plastic and metal.

The array transducer 506 functions as a piezoelectric element and has a plurality of piezoelectric elements 520 arranged in an array. The piezoelectric elements 520 are transducing elements which transduce electricity to pressure and pressure to electricity, and are capable of transmitting ultrasonic waves and receiving reflected ultrasonic waves X which are reflected from the flaw 504 and the like in the object 503 to be inspected.

The reflector 513, which functions as a reflecting section, reflects an ultrasonic wave transmitted from a predetermined piezoelectric element 520 to change a propagation direction thereof so as to make the ultrasonic wave incident from a side of the object 503 to be inspected.

The couplant 507 is a medium for improving an acoustic coupling state between the shoe member 505 and the array transducer 506, and a semifluid acoustic medium having appropriate viscosity, for example, glycerin is usually used. The couplant 507 is interposed between the shoe member 505 and the array transducer 506 so that the ultrasonic wave can be efficiently transmitted between the shoe member 505 and the array transducer 506, and reflection (a kind of noise) of the ultrasonic wave on an interface of each of the shoe member 505 and the array transducer 506 is reduced.

The transmission/reception switching device 508 is a device performing selection of elements which are to transmit and receive ultrasonic waves, from the plural piezoelectric elements 520 in the array transducer 506, and so on, and has a driven element selecting section 521, a signal generating section 522, a signal detecting circuit 523, and an amplifier 524.

The driven element selecting section 521 functions as a signal generating circuit, and is a selecting circuit to which electrical signals generated by the signal generating section 522 are inputted and which selects the piezoelectric elements 520 to generate the ultrasonic waves.

The signal generating section 522 is intended for generating the electrical signals for causing the piezoelectric elements 520 to generate the ultrasonic waves, and usually includes an oscillation circuit.

The signal detecting circuit 523, which functions as a detecting section, is a detecting circuit detecting the electrical signals that the respective piezoelectric elements 520 generate as a result of receiving the ultrasonic waves. In this detection, the selection of the piezoelectric elements 520 is possible as necessary, and the electrical signals corresponding to the selected piezoelectric elements 520 are sent to an amplifier 524. At this time, the plural piezoelectric elements 520 are selectable, thereby further enhancing a parallel characteristic of signal processing.

The amplifier 524 is intended for amplifying the signals detected by the signal detecting circuit 523, and has the amplifying elements in number corresponding to the number of outputs from the signal detecting circuit 523 (the number of the selected piezoelectric elements 520).

In short, the transmission/reception switching device 508 selects the receiving elements which are to receive the reflected ultrasonic waves X (ultrasonic wave echoes X), from the piezoelectric elements 520, and after amplifying electrical signals E generated by the selected piezoelectric elements 520, the transmission/reception switching device 508 transmits the amplified electrical signals E in sequence to the image synthesizing device 509.

The image synthesizing device 509, which functions as an image creating section creating an image, has an A/D converter 525 and an parallel processor 526. The A/D converter 525 analog/digital converts the electrical signals received in the signal detecting circuit 523.

The parallel processor 526, which functions as a sonic velocity correcting section and an image creating section, is a signal processing section which performs signal processing for visualizing a state of an inspection object based on the signals digitized by the A/D converter 525.

The display device 510 is a display device displaying information led from the image synthesizing device 509, and for example, CRT, a liquid crystal display are usable.

(Operation of Ultrasonograph)

Hereinafter, the operation of the ultrasonograph will be explained.

(1) Triggered by the electrical signals inputted to the piezoelectric elements 520 from the signal generating section 522 via the driven element selecting section 521, the piezoelectric elements 520 transmit the ultrasonic waves. The ultrasonic waves transmitted from the piezoelectric elements 520 reach the flaw 504 inside the object 503 to be inspected via the shoe member 505 and the water 502. The ultrasonic waves are reflected on the flaw 504 so that they turn to the reflected ultrasonic waves X, which are received by the piezoelectric elements 520 again via the water 502 and the shoe member 505.

(2) The electrical signals which are generated from the respective piezoelectric elements 520 based on the received ultrasonic waves X are detected, amplified, digitized by the signal detecting circuit 523, the amplifier 524, and the A/D converter 525, and thereafter, the parallel processor 526 performs image synthesizing for these electrical signals.

This image synthesizing can be conducted by aperture synthesizing, using transmission/reception propagation time td from the transmission to the reception of the ultrasonic waves and intensities (amplitude values) Ad of the reflected ultrasonic waves X.

Specifically, an ultrasonic wave reflection source (for example, the flaw 504) of the object 503 to be inspected exists on an elliptical surface with a fixed distance corresponding to the transmission reception propagation time td (equal distance propagation surface 512), the ellipse having focuses thereof at a transmission position and a reception position of the ultrasonic wave, and therefore, the intersection position of the ellipses corresponding to different transmission positions and reception positions is the position of the reflection source so that, when ellipses corresponding to the combinations of many transmission positions (piezoelectric elements 520) and reception positions (piezoelectric elements 520) are overlapped (added), for example, on a three-dimensional image memory, the inside of the object 503 to be inspected can be reconstructed.

Specifically, the equal distance propagation surface 512 corresponding to the transmission/reception propagation time td is calculated for each pair of the piezoelectric elements 520 which are selected on the transmitting side and the receiving side respectively, and the amplitude value Ad of the reflecting ultrasonic wave X is added on the calculated equal distance propagation surface 512. The plural equal distance propagation surfaces 512 respectively corresponding to the combinations of the piezoelectric elements 520 selected on the transmitting side and the receiving side respectively are calculated and the amplitude values of the reflected ultrasonic waves X on the plural equal distance propagation surfaces 512 are added so that an image of the object 503 to be inspected including the flaw 504 and so on therein can be generated.

The transmission/reception propagation time td is the time required from the transmission of the ultrasonic wave to the reception of the reflecting ultrasonic wave X, and it is a difference (t2−t1) between time t1 when the ultrasonic wave is transmitted from the piezoelectric element 520 on the transmitting side and time t2 when the ultrasonic wave is received by the piezoelectric element 520 on the receiving side.

(3) When the equal distance propagation surface 512 is calculated from the transmission/reception propagation time td, it is preferable that refraction on both interfaces, namely, "the interface between the shoe member 505 and the water 502" and "the interface between the object 503 to be inspected and the water 502" is taken into consideration. Specifically, in consideration of Snell's formulas represented by the following formulas (1), (2), the equal distance propagation surface 512 is calculated more precisely.

$$C5/\sin\theta 52 = C2/\sin\theta 25 \quad \text{Formula (1)}$$

$$C2/\sin\theta 23 = C3/\sin\theta 32 \quad \text{Formula (2)}$$

where,

C5: velocity of the ultrasonic wave in the shoe member 505
C2: velocity of the ultrasonic wave in the water 502
C3: velocity of the ultrasonic wave in the object 503 to be inspected
θ52: an incident (exit) angle of the ultrasonic wave from the shoe member 505 to the water 502
θ25: an exit (incident) angle of the ultrasonic wave from the shoe member 505 to the water 502
θ23: an incident (exit) angle of the ultrasonic wave from the water 502 to the object 503 to be inspected
θ32: an exit (incident) angle of the ultrasonic wave from the water 502 to the object 503 to be inspected (4) The ultrasonic wave transmitted from the piezoelectric element 520 is reflected in a horizontal direction on the reflector 513 fixed in the container 501 so that a horizontal direction measuring ultrasonic wave Z can be made incident on a side face of the object 503 to be inspected. This horizontal direction measuring ultrasonic wave Z is reflected on the side face of the object 503 to be inspected, the flaw 504 therein, and so on to be received by the piezoelectric element 520 so that it can be used for the image synthesizing in the parallel processor 526.

Data on the horizontal direction measuring ultrasonic wave Z is thus taken in so that horizontal position measurement of the side face of the object 503 to be inspected and the flaw 504 therein or imaging from the horizontal direction can be performed at the same time.

When the piezoelectric elements 520 transmitting and receiving this horizontal direction measuring ultrasonic wave Z are discriminated from the piezoelectric elements 520 transmitting and receiving the reflected ultrasonic waves X, discrimination between front-direction images of the object 503 to be inspected based on the reflected ultrasonic waves X and side direction images of the object 503 to be inspected based on the horizontal direction measuring ultrasonic wave Z is facilitated. Further, at the time of display on the display device 510, when the front images and the side images thus discriminated are displayed in different display colors, image discrimination can be facilitated.

(5) Since the sonic velocity in the water 502 varies depending on water temperature and so on, correction of the ultrasonic velocity makes it possible to create more precise images.

A value of the ultrasonic velocity itself in the water 502 may be inputted to the image synthesizing device 509 and stored therein for making this correction, but this correction can be also made based on the transmission/reception propagation time td of the reflecting ultrasonic wave X from the surface of the object 503 to be inspected or the fixing stand.

Supposing that a thickness d5 of the shoe member 505, a distance L from the shoe member 505 to the surface of the object 503 to be inspected, and a sonic velocity C5 in the shoe member 505 are known, a sonic velocity C2 in the water 502 can be calculated by the following formula (3).

$$td = 2\cdot(d5/C5) + 2\cdot(L/C2) \quad \text{Formula (3)}$$

Here, when the surface of the object 503 to be inspected is extracted by image analysis of the synthesized image based on the characteristic of surface shape (for example, planar surface, curved surface) of the object 503 to be inspected, automatic correction of the sonic velocity in the water 502 is made possible. Specifically, the synthesized image is binarized or the like so that the contour of the object 503 to be inspected is extracted, a point near the piezoelectric element 520 is selected from this contour, and the transmission/reception propagation time td corresponding to this point is obtained, thereby correcting the sonic velocity C2 in the water 502.

EIGHTH EMBODIMENT

FIG. 12 is a schematic diagram explaining the configuration of an ultrasonograph according to an eighth embodiment of the present invention. As shown in this drawing, this ultrasonograph uses an array transducer 506 exclusively for reception and has an additional shoe member 545 and transmission array transducer 546 which is fixedly in close contact with the shoe member 545 via a couplant 547.

The shoe member 545 is a solid acoustic medium having a flat plate structure which is fixed in water 502 at a position across an object 503 to be inspected relative to a shoe member 505 so as to be parallel to a surface of the shoe member 505, and the same material as that of the shoe member 505 is usable therefor.

The transmission array transducer 546 has a plurality of piezoelectric elements 540 arranged in an array, which is the same structure as that of the array transducer 506.

The couplant 547 is a medium for improving an acoustic coupling state between the shoe member 545 and the array transducer 546, and the same material as that of the couplant 507 is usable therefor.

Hereinafter, the operation of the ultrasonograph according to the eighth embodiment will be explained.

A transmission/reception switching device 508 selects and drives a specific piezoelectric element 540 out of the plural piezoelectric elements 540 in the array transducer 546, and ultrasonic waves U are transmitted from the selected and driven piezoelectric element 540. The transmitting ultrasonic waves U transmit inside the shoe member 545, the water 502, and the object 503 to be inspected and are further received by the array transducer 506 via the water 502 and the shoe member 505. Electrical signals E generated by the plural piezoelectric elements 520 are selectively detected by a transmission/reception switching device 508. An image synthesizing device 509 synthesizes a transmission image of the object 503 to be inspected from the detected electrical signals E, and the display device 510 displays the synthesizing result of the synthesized transmission image.

As a result, the inside of the object 503 to be inspected in the water 502 can be visualized while the array transducer 506 is kept disposed outside the container 501.

The image synthesizing in the image synthesizing device 509 is performed based on transmission/reception propagation time and amplitude values of the transmitting ultrasonic waves U. When there exists a medium (for example, the object 503 itself to be inspected or an internal structure such as a flaw 504) different from the water 502 in routes of the ultrasonic waves from the transmitting piezoelectric element 540 to the receiving piezoelectric elements 520, the ultrasonic waves are reflected on an interface thereof (for example, a surface of the object 503 to be inspected, a flaw 504, or the like) so that the amplitude of the received ultrasonic waves U is reduced. Further, the transmitting ultrasonic waves U pass inside the medium so that the transmission/reception propagation time varies. The transmission/reception propagation time and the amplitude values of the transmitting ultrasonic waves U corresponding to the routes of the ultrasonic waves (ultrasonic wave transmission routes) from the transmitting piezoelectric element 540 to the receiving piezoelectric elements 520 are thus computed, so that the transmission image of the flaw 504 inside the inspection object 503 can be synthesized.

The calculation of the ultrasonic wave transmission routes is conducted based on a positional relationship between the transmitting piezoelectric elements 540 and the receiving piezoelectric elements 520. When refraction on "an interface between the shoe member 505 and the water 502" and "an interface between the shoe member 545 and the water 502" is taken into consideration in calculating the ultrasonic wave transmission routes, the ultrasonic wave transmission routes can be calculated more precisely. This means that the Snell's formulas such as the formulas (1), (2) are appropriately taken into consideration.

INDUSTRIAL APPLICABILITY

An ultrasonograph, an ultrasonic transducer, an inspection device, and an ultrasonic imaging device according to the present invention can be manufactured in the electronic device manufacturing industry, the electronic device manufacturing industry, the measuring instrument manufacturing industry, and so on, and can be used in the automobile part manufacturing industry, the manufacturing industry of various materials, the semiconductor device manufacturing industry, the engineering industry, and so on. Therefore, they have industrial applicability.

What is claimed is:

1. An ultrasonograph comprising:
   a laser beam source generating an intermittent laser beam;
   an optical transmitter irradiating an inspection object with the generated intermittent laser beam in a spot-like state;
   a scan-moving mechanism scan-moving the optical transmitter relatively to the inspection object;
   a vibration displacement detecting section which performs non-contact detection of vibration displacement on a surface of the inspection object by a displacement measuring method using a laser beam, the vibration displacement caused by an echo of an ultrasonic wave in the inspection object generated by the irradiated laser beam, and which transduces the vibration displacement to an electrical signal; and
   a processing section which performs processing for visualizing a state of the inspection object based on the electrical signal obtained after the transducing and a position of the scan-moved optical transmitter.

* * * * *